US009782116B2

(12) United States Patent
Lonis

(10) Patent No.: US 9,782,116 B2
(45) Date of Patent: Oct. 10, 2017

(54) STABILITY-ASSESSING SYSTEM

(71) Applicant: Justin Michael Lonis, Mentor, OH (US)

(72) Inventor: Justin Michael Lonis, Mentor, OH (US)

( * ) Notice: Subject to any disclaimer, the term of this patent is extended or adjusted under 35 U.S.C. 154(b) by 24 days.

(21) Appl. No.: 14/702,237

(22) Filed: May 1, 2015

(65) Prior Publication Data
US 2016/0007903 A1     Jan. 14, 2016

Related U.S. Application Data

(60) Provisional application No. 62/023,646, filed on Jul. 11, 2014, provisional application No. 61/987,091, filed on May 1, 2014.

(51) Int. Cl.
*A61B 5/00*     (2006.01)
*A61B 5/11*     (2006.01)

(52) U.S. Cl.
CPC .......... *A61B 5/4023* (2013.01); *A61B 5/6892* (2013.01); *A61B 5/0002* (2013.01); *A61B 5/11* (2013.01); *A61B 5/7445* (2013.01); *A61B 5/7475* (2013.01); *A61B 2562/0219* (2013.01); *A61B 2562/0247* (2013.01)

(58) Field of Classification Search
CPC ....... A61B 5/11; A61B 5/1101; A61B 5/1102; A61B 5/1116; A61B 5/1121; A61B 5/1124; A61B 5/4023; A61B 5/6892; A61B 5/7445
See application file for complete search history.

(56) References Cited

U.S. PATENT DOCUMENTS

| | | | | |
|---|---|---|---|---|
| 3,712,294 A * | 1/1973 | Muller | ................. | A61B 5/1036 116/34 A |
| 5,603,334 A * | 2/1997 | Sharp | .................... | A61B 5/103 482/146 |
| 5,613,690 A * | 3/1997 | McShane | ............... | A63B 22/18 273/449 |
| 5,830,158 A * | 11/1998 | Zanakis | ............... | A61B 5/1036 600/595 |
| 6,063,046 A * | 5/2000 | Allum | .................. | A61B 5/1036 600/595 |
| 6,602,210 B2 * | 8/2003 | Savet | ................... | A61B 5/1036 600/595 |
| 6,607,497 B2 * | 8/2003 | McLeod | .............. | A61B 5/1036 600/595 |
| 7,955,279 B2 * | 6/2011 | Berthonnaud | ....... | A61B 5/4023 382/132 |
| 8,315,823 B2 * | 11/2012 | Berme | .................... | G01L 25/00 702/101 |
| 8,622,747 B2 * | 1/2014 | Chu | .................. | A63B 22/0292 434/258 |

(Continued)

*Primary Examiner* — Max Hindenburg
(74) *Attorney, Agent, or Firm* — Wegman, Hessler & Vanderburg

(57) ABSTRACT

A system for assessing the stability of a person relative to a horizontal surface during an assessment session is provided. The system includes a platform having a stage upon which the person stands. A sensing configuration senses when the person is unbalanced on the stage, and conveys this information to a processor. The processor converts this information into meaningful graphics for viewing on a display.

23 Claims, 47 Drawing Sheets

(56) References Cited

U.S. PATENT DOCUMENTS

| | | | | |
|---|---|---|---|---|
| 8,764,532 B1* | 7/2014 | Berme | ................... | A61B 5/742 |
| | | | | 434/258 |
| 9,149,222 B1* | 10/2015 | Zets | ......................... | A61B 5/16 |
| 9,241,637 B2* | 1/2016 | Wiard | ................ | A61B 5/02125 |

* cited by examiner

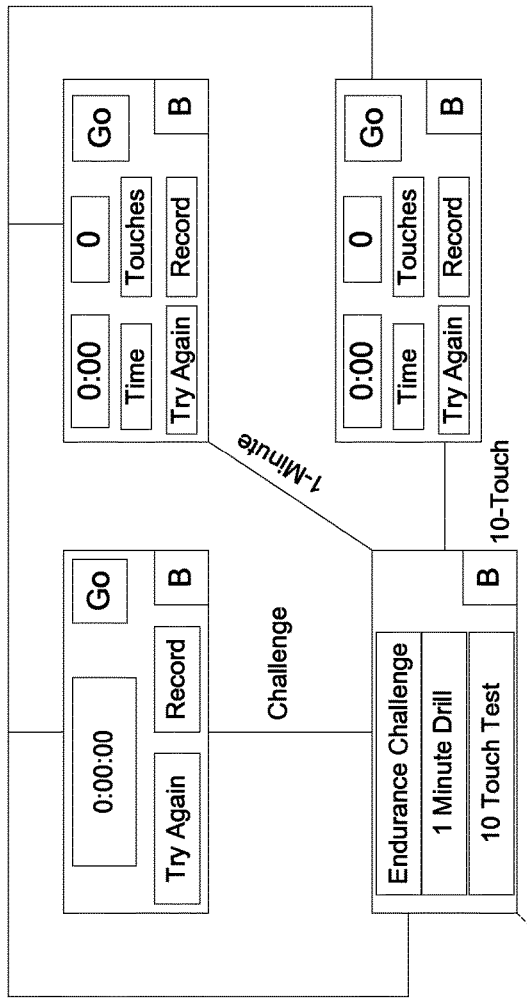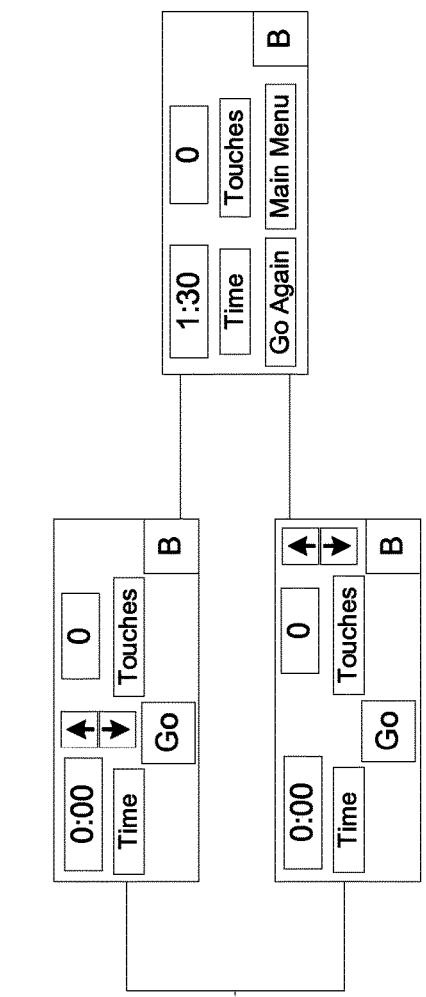
FIGURE 6C

STABILITY-ASSESSING SYSTEM

CROSS-REFERENCE TO RELATED APPLICATIONS

This application claims benefit of U.S. Provisional Patent Application Ser. No. 62/023,646 filed on Jul. 11, 2014; and U.S. Provisional Patent Application Ser. No. 61/987,091 filed on May 1, 2014, both of which are herein incorporated by reference in their entireties.

BACKGROUND OF THE INVENTION

There are numerous injuries, conditions and disorders in which it is beneficial to assess the stability and/or balance of a person. Traditional balance boards can be used for assessing the stability of a person relative to a horizontal surface (e.g., the floor). Traditional balance boards include a platform, which can pivot, wobble or rock, on which a user can stand in an effort to maintain his/her balance so that the platform does not touch the ground.

SUMMARY OF THE INVENTION

A stability-assessing system comprises features allowing it to offer improved procedures for analyzing ankle injuries, evaluating ankle strength, and/or for indicating the likelihood of a concussion. The system can be used as a warm-up device any lower body extremity or any person looking to improve gross instability. The system can be used to analyze neuromuscular weakness for any ankle or lower body extremities, evaluating ankle and/or lower body strength and/or allowing for baseline data to be established to see if an athlete has a predisposition for an injury or to aid in the indication, likelihood or recognition of a concussion or concussion related injury.

The stability-assessing device and system can also be used in a performance or exercise mode. In this mode, the system provides indications or instructions to a user to perform a set of movements according to a predefined program.

One aspect of the disclosed technology relates to a stability-assessing device for assessing the stability of a person relative to a horizontal surface, the device including a platform having a generally planar top surface, the platform having a perimeter; a base disposed below and supporting the platform, the base having a generally non-planar bottom surface such that the platform will rotate in response to a weight imbalance on the platform; a sensing configuration integrated into the device, wherein the sensing configuration is configured to sense orientation and/or motion of the platform relative to the horizontal surface and to generate signals representative of the sensed orientation and/or motion of the platform relative to the horizontal surface; and wherein the platform is electronically divided into zones around the perimeter of the platform.

According to one feature, the sensing configuration is configured to sense orientation and/or motion of each zone of the platform.

According to one feature, wherein the sensing configuration includes one or more sensors associated with each zone and configured to sense orientation and/or motion of each zone of the platform relative to the horizontal surface.

According to one feature, the sensors include pressure sensors, force sensors, acceleration sensors, tilt sensors and/or bump sensors.

According to one feature, the platform is electronically divided into at least four zones.

According to one feature, the platform is electronically divided into at least eight zones.

According to one feature, the sensor configuration is configured to detect when a portion of the perimeter of the platform corresponding to one of the electrically defined zones contacts the horizontal surface.

According to one feature, the sensor configuration is configured to detect the force with which a portion of the perimeter of the platform corresponding to one of the electrically defined zones contacts the horizontal surface.

According to one feature, the sensor configuration includes a plurality of sensors within the platform configured to detect a person's weight distribution when the user is on the platform.

According to one feature, the stability-assessing device includes a visual indicator configuration integrated into the device, wherein the visual indicator configuration is configured to provide selective visual indications to one or more of the electronically defined zones.

According to one feature, the visual indication configuration includes a light-emitting diode (LED) assembly associated with each of the electronically defined zones.

According to one feature, the stability-assessing device includes a controller operatively coupled to the sensing configuration and the visual indicator configuration, wherein the controller is configured to provide command signals to the visual indicator configuration, and to receive signals from the sensing configuration.

According to one feature, the controller is configured to provide a command signal to the visual indicator configuration associated with a given zone upon receiving a signal from the sensing configuration indicative of a sensed orientation with respect to the given zone.

According to one feature, the stability-assessing device includes a display positioned in the platform.

According to one feature, the display is a touch-sensitive display.

According to one feature, the stability-assessing device includes a wireless communication interface operatively coupled to the controller.

According to one feature, a stability-assessing system including a stability-assessing device in wireless data communication with a remote display.

According to one feature, the controller is programmed to convert input from the sensor configuration into balance characteristics particular to each zone.

Another aspect of the disclosed technology relates to a balance board for use by a person on a horizontal surface. The balance board includes a platform having a generally planar top surface, the platform having a perimeter; a base disposed below and supporting the platform, the base having a generally non-planar bottom surface such that the platform will rotate in response to a weight imbalance on the platform; a sensing configuration integrated into the balance board, wherein the sensing configuration is configured to sense orientation and/or motion of the platform relative to the horizontal surface and to generate signals representative of the sensed orientation and/or motion of the platform relative to the horizontal surface; wherein the platform is electronically divided into zones around the perimeter of the platform; and a visual indicator configuration integrated into the device, wherein the visual indicator configuration is configured to provide selective visual indications to one or more of the electronically defined zones.

According to one feature, the visual indication configuration includes a light-emitting diode (LED) assembly associated with each of the electronically defined zones.

According to one feature, the balance board includes a controller operatively coupled to the sensing configuration and the visual indicator configuration, wherein the controller is configured to provide command signals to the visual indicator configuration, and to receive signals from the sensing configuration, the command signals resulting in selective visual indications in one or more of the zones, and to receive signals from the sensing configuration.

According to one feature, the controller is configured to provide command signals to the visual indicator configuration in a predefined pattern.

According to one feature, the balance board includes a display positioned in the platform.

According to one feature, the balance board includes a wireless communication interface operatively coupled to the controller.

These and further features of the disclosed technology will be apparent with reference to the following description and attached drawings. In the description and drawings, particular embodiments or aspects of the disclosed technology have been disclosed in detail as being indicative of some of the ways in which the principles of the disclosed technology may be employed, but it is understood that the disclosed technology is not limited correspondingly in scope. Rather, the disclosed technology includes all changes, modifications and equivalents coming within the spirit and terms of the claims appended thereto.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF SEVERAL VIEWS OF THE DRAWINGS

These and other features of the disclosed technology, and their advantages, are illustrated specifically in embodiments of the disclosed technology now to be described, by way of example, with reference to the accompanying diagrammatic drawings, in which:

FIG. 4O is an exemplary visual representation of information collected using a stability-assessing system in accordance with one aspect of the disclosed technology.

FIGS. 6A-6C provide a diagrammatic illustration of an exemplary user interface and method of operation in accordance with one aspect of the disclosed technology;

Figure 1A:
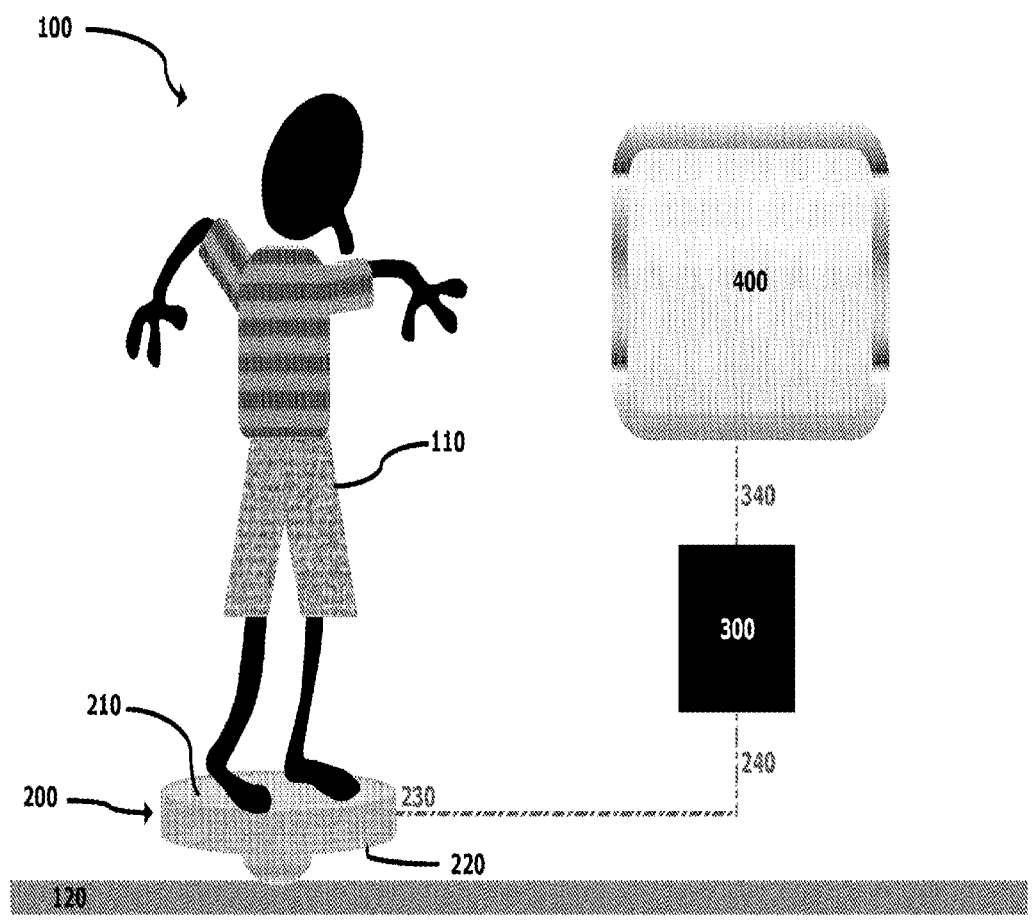
FIG. 1A is a diagrammatic illustration of a stability-assessing system in accordance with one aspect of the disclosed technology.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION OF EMBODIMENTS

There are numerous injuries, conditions and disorders in which it is beneficial to assess the stability and/or balance of a person. Aspects of the disclosed technology recognize that it can be difficult for physiotherapists or other clinicians to effectively rehabilitate or otherwise treat patients with traditional balance boards. Aspects of the disclosed technology provide a stability-assessing device and system in which an integrated sensor configuration can detect various movements of a user on the stability-assessing device. Other aspects of the disclosed technology provide a device and system in which a stability-assessing device provides instructions or commands to a user to perform a certain set of balance-related movements according to one or more predefined patterns.

Referring now to FIGS. 1A-1C and FIGS. 2A-2C, a stability-assessing system 100 is provided for assessing the stability of a person 110 relative to a horizontal surface 120. The system 100 includes a stability-assessing device (also referred to as a balance board) 200 having a top surface (also referred to as a stage or a platform) 210 and a base 260. In accordance with one embodiment, the top surface 210 is a generally planar top surface and the base 260 is a generally non-planar surface (e.g., a curved or bowed surface). It will be appreciated that the term "generally planar" is intended to include surface features on the platform, such as texture or surface features to provide traction and other accessories or sensors extending upward from the platform.

It also will be appreciated that the top portion 210 and the base 260 of the stability-assessing device can be made of a number of suitable materials without departing from the disclosed technology. For example the stability-assessing device can be made from one or more materials, including wood, plastics, composite materials, metals, hardened glass or any combination thereof. In the illustrated embodiment, the top surface or stage is generally circular in shape. Alternatively, the top surface may take on any polygonal shape.

Figure 1B:
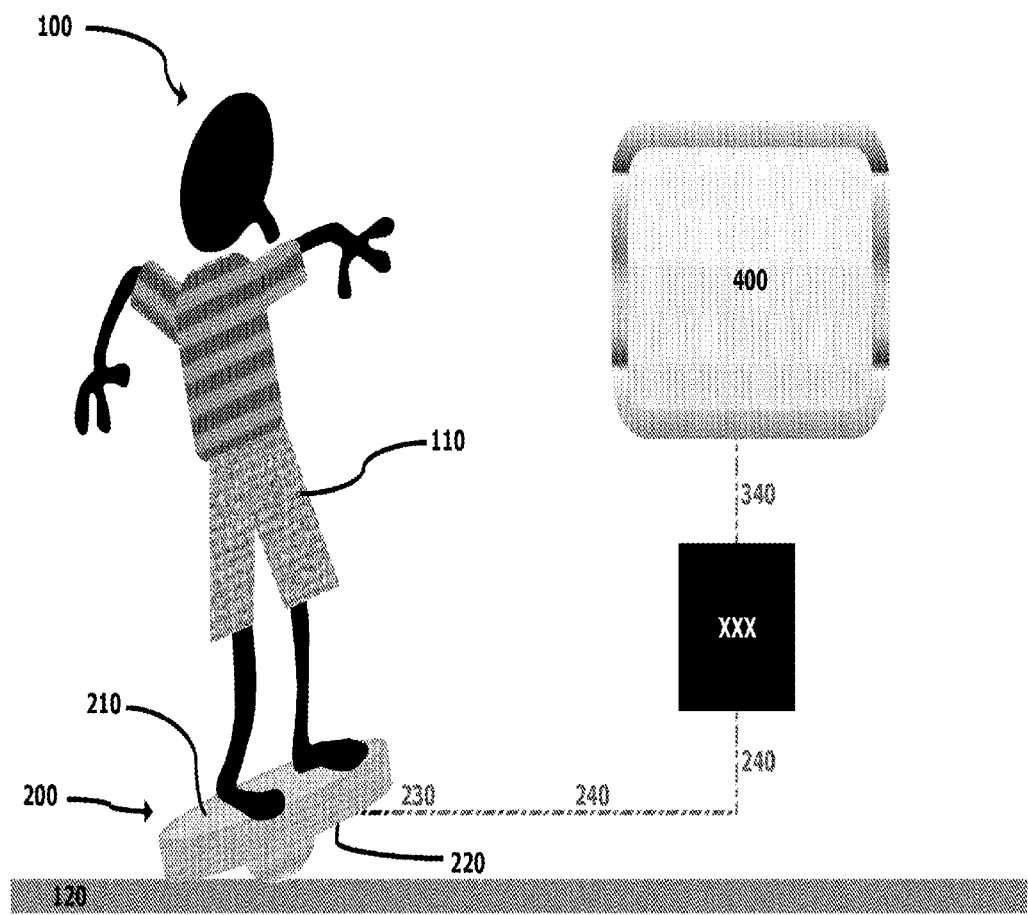
FIG. 1B is a diagrammatic illustration of a stability-assessing system in accordance with one aspect of the disclosed technology.
Figure 1C:
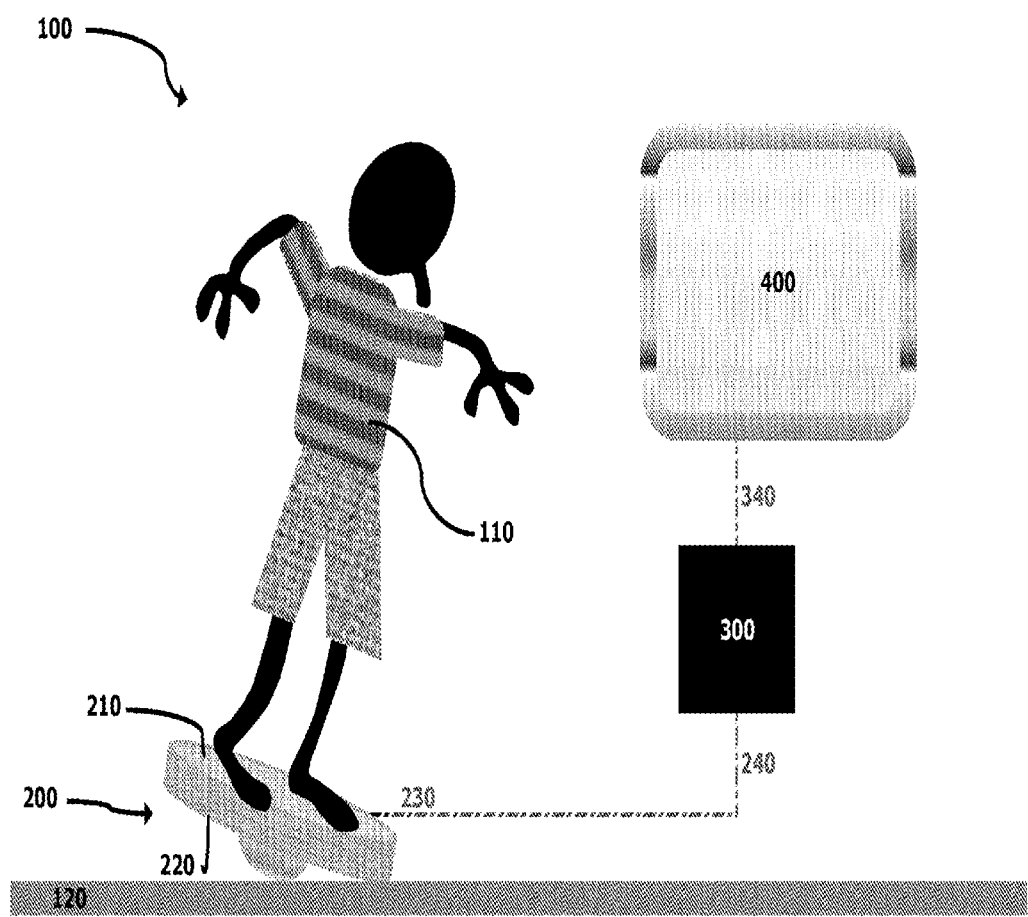
FIG. 1C is a diagrammatic illustration of a stability-assessing system in accordance with one aspect of the disclosed technology.

It will be appreciated that the base may be integrally formed with the stage. Alternatively, the base may be formed separately and attached to the stage. As shown in FIG. 1A-1C, the stability-assessing device includes a platform and a base operatively coupled to the platform 210 such that the base 260 will rest on the ground during normal operation and the platform 210 will be supported above the ground. The base 260 is configured to support the platform 210 in a manner where the platform will rotate or otherwise pivot in response to a weight imbalance on the platform 210. While the base 260 is shown having a generally round curved lower surface it will be appreciated that the base 260 can take on other geometries without departing from the scope of the disclosed technology, provided that the geometry of the base allows the device to rotate or otherwise pivot in response to a weight imbalance on the platform.

In the illustrated embodiment, FIG. 1A shows the device 200 with the person in a relatively balanced state (e.g., with the platform generally parallel to the horizontal surface and/or without a perimeter of the platform in contact with the horizontal surface. Conversely, FIGS. 1B-1C shows the device with the person in a relatively unbalanced state (e.g., with the platform at an angle relative to the horizontal surface greater than a predefined threshold and/or with a portion of the perimeter in contact with the ground.)

With continued reference to FIGS. 1A-1C, and stated differently from the above description, a system 100 is provided for assessing the stability of a person 110 relative to a horizontal surface 120 (e.g., the floor). This system 100 can be used, for example, to analyze an ankle injury, to evaluate ankle strength, and/or to indicate the likelihood of a concussion. As will be discussed in more detail below, in accordance with certain embodiments, the system 100 can be used in a performance or exercise mode.

In the illustrated embodiment, the system 100 includes a platform 200 having stage 210, elevated above the horizontal surface 120, upon which the person 110 stands. The platform 200 also has a circumferential rim 220 below the stage 210 and above the horizontal surface 120. When the person 110 is balanced on the stage 210, the circumferential rim 220 does not contact the horizontal surface 120. (FIG. 1A.) When the person 110 is unbalanced on the stage 210, the circumferential rim 220 is contacts the horizontal surface 120. (FIGS. 1B and 1C.)

A sensing structure 230 senses when the circumferential rim 220 contacts the horizontal surface 120. Data compiled by the sensing structure 230 is conveyed, via communication course 240, to a processor (also referred to as a controller) 300. The processor 300 compiles, interpret, and/or otherwise construes the data. The processed data is output in a meaningful fashion, via communication course 340, to display 400.

The stability-assessing device is formed with integrated electronics. In accordance with one embodiment, the electronics are integrated into the platform or top portion of the stability-assessing device. Although it will be appreciated that one or more electronic components can be incorporated into the base without departing from the scope of the disclosed technology.

In the illustrated embodiment, the platform includes a perimeter or circumferential rim that can be divided into a plurality of zones around the perimeter. While the device may include visual indications of the plurality of zones, in operation the device will be electronically divided or segmented into a plurality of zones around the perimeter of the platform. The device will include a number of sensors allowing for detection and measurement of tilting or pivoting of the board as well as the amount of force that occurs when the board hits the ground (e.g., when a portion of the perimeter or circumferential rim hits the ground).

In accordance with one embodiment, the sensor configuration can include pressure or force sensors. Alternatively or additionally, the sensor configuration can include one or more accelerometers, tilt sensors, inclinometers, gyroscopes and/or bump sensors, or the like. Stated differently, the platform includes one or more sensors configured to sense orientation and/or motion of the platform and generates signals representative of or otherwise indicative of the sensed motion.

In accordance with one embodiment, the stability-assessing device includes one or more visual indicators (e.g., light-emitting diodes (LEDs)) (also referred to as a visual indicator configuration) that provide visual indications in response to predefined conditions. For example, the visual indicators can emit light when a segment or portion of the platform touches the ground or tilts past a predefined angle which is measured by the integrated tilt sensors. As is discussed more fully below, the sensor configuration can be configured to detect and measure "vibrations" of the board when a portion of it hits the ground and the accelerometer data can be tracked and also used as an indicator.

The harder the board hits the ground, as well as the speed of acceleration back and forth, can be measured and tracked to detect when a participant has symptoms of a concussion, such that his or her proprioception is abnormal or otherwise weakened or that the participant might have neuromuscular/neuroskeletal weakness. It will be appreciated that this information can also be used in conjunction with detection and treatment of other diseases, such as Parkinson's disease, cerebral palsy, multiple sclerosis, and the like.

In accordance with one embodiment, each segment or zone of the board or platform will include a sensing configuration as well as a visual indication configuration (designated general as 231-238). The sensing configuration and visual indication configuration for each segment will be in data communication with a processor or controller. In one embodiment, the processor or controller is integrated within the balance-assessing device. Alternatively, the commands or data to and from the sensing configuration and/or visual indication configuration can be communicated to a remote processor (e.g., through a wired connection or a wireless connection).

In accordance with one exemplary embodiment, the device can be configured to include one or more weight sensors integrated within the platform such that based on where the user's foot is placed on the platform, the user's weight distribution can be measured to determine if more weight is on the front or back of the user's foot during a variety of detected board touches. For example when the board touches the ground in each of the electronically defined segments, does the user place more weight on the front or back of the foot during certain touches. Stated differently, the weight sensor configuration can help to determine weight and distribution shift as the board touches a particular segment. In one exemplary embodiment, the sensor configuration could include a sensor array within a six inch by twelve inch space employing several hundred sensors with real time pressure profiling in a pressure range of about 0.5 to about 32 psi and a spatial resolution of about 10 to about 15 millimeters.

Figure 2A:
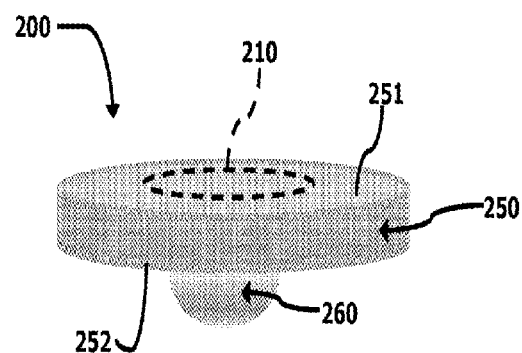
FIG. 2A is a side perspective view of a stability-assessing device in accordance with one aspect of the disclosed technology.
Figure 2B:
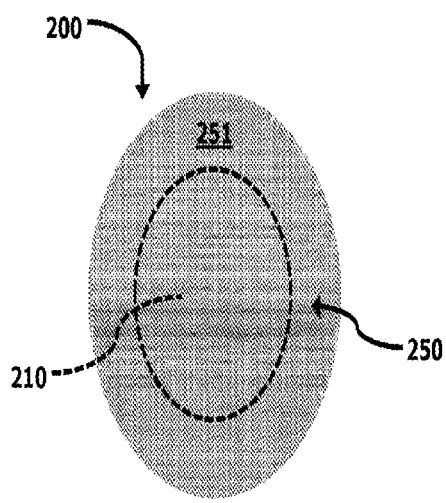
FIG. 2B is a top view of a stability-assessing device in accordance with one aspect of the disclosed technology.
Figure 2C:
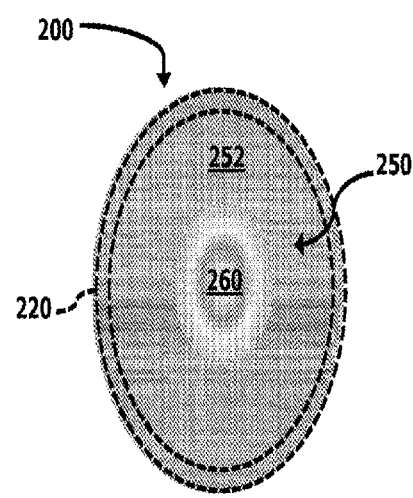
FIG. 2C is a bottom view of a stability-assessing device in accordance with one aspect of the disclosed technology.

The platform 200 can be constructed from a disc-shaped dais 240 and a bowed base 250. (FIGS. 2A-2C.) The stage 210 can be situated on the flat upper side 241 of the dais 240 and the rim 220 can be situated around the circumference of flat lower side 242 of the dais 240. The base 250 is attached to the center of the lower side 242 of the dais 240, with its bowed underside causing the dais 240 to tilt absent balancing on the stage 210.

The circumferential rim 220 can be divided into a plurality of zones 221-228. (FIGS. 2D-2G.) In the illustrated platforms 220, the rim 220 includes eight zones 221-228. However, platforms having fewer zones (i.e., seven, six, five, four, three, etc.) or more zones (i.e., nine, ten, eleven, twelve, etc.) also are contemplated, and may be desirable.

The sensing configuration 230 can be adapted to sense which zone 221-228 is contacting the horizontal surface 120 when an imbalance occurs. Specifically, for example, a sensor 231-238 can be associated with each zone 221-228 whereby it be will be triggered upon the respective zone contacting the horizontal surface 120. The sensors 231-238 can be, for example, touch sensors, pressure sensors, acceleration sensors, and/or tilt tracking sensors.

Figure 2D:
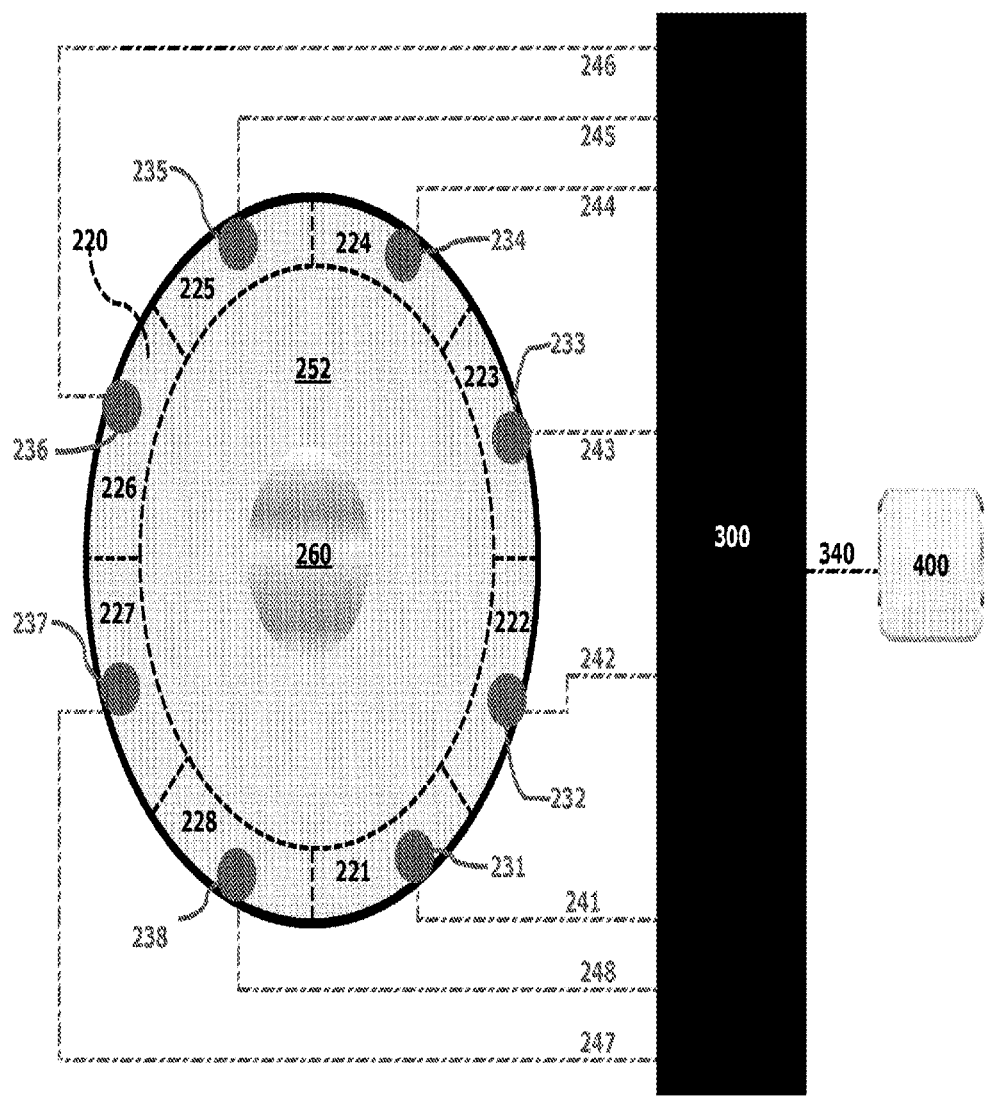
FIG. 2D is a diagrammatic illustration of a stability-assessing system including exemplary sensors in accordance with one aspect of the disclosed technology.

As indicated above, the sensing configuration 230 electrically communicates with the processor or controller 300 via a communication course 240. This course can be accomplished via individual communication lines 241-248 associated with each sensor 231-238. (FIG. 2D.) Each communication line 241-248, which can be wired or wireless, sends a separate signal to the processor 300 regarding the respective sensor 231-232.

Figure 2E:
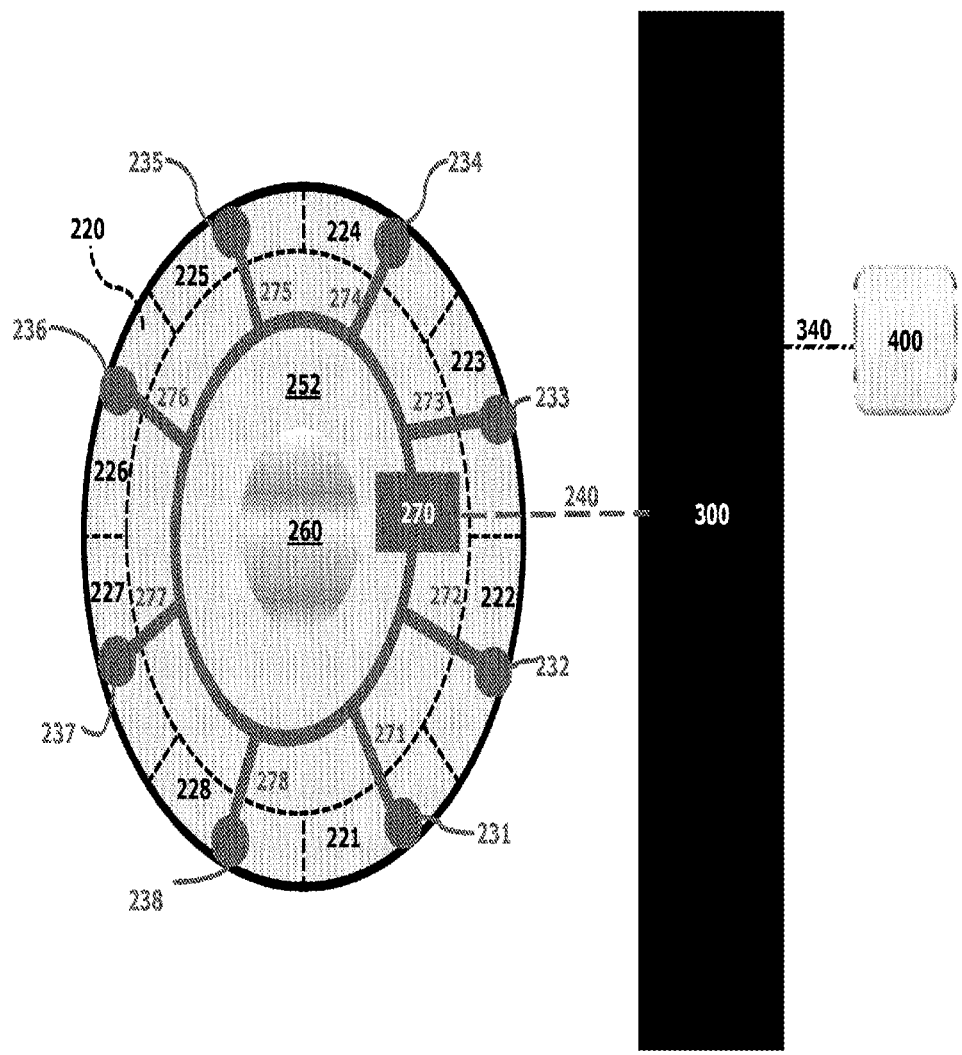
FIG. 2E is a diagrammatic illustration of a stability-assessing system including exemplary sensors in accordance with one aspect of the disclosed technology.
Figure 2F:
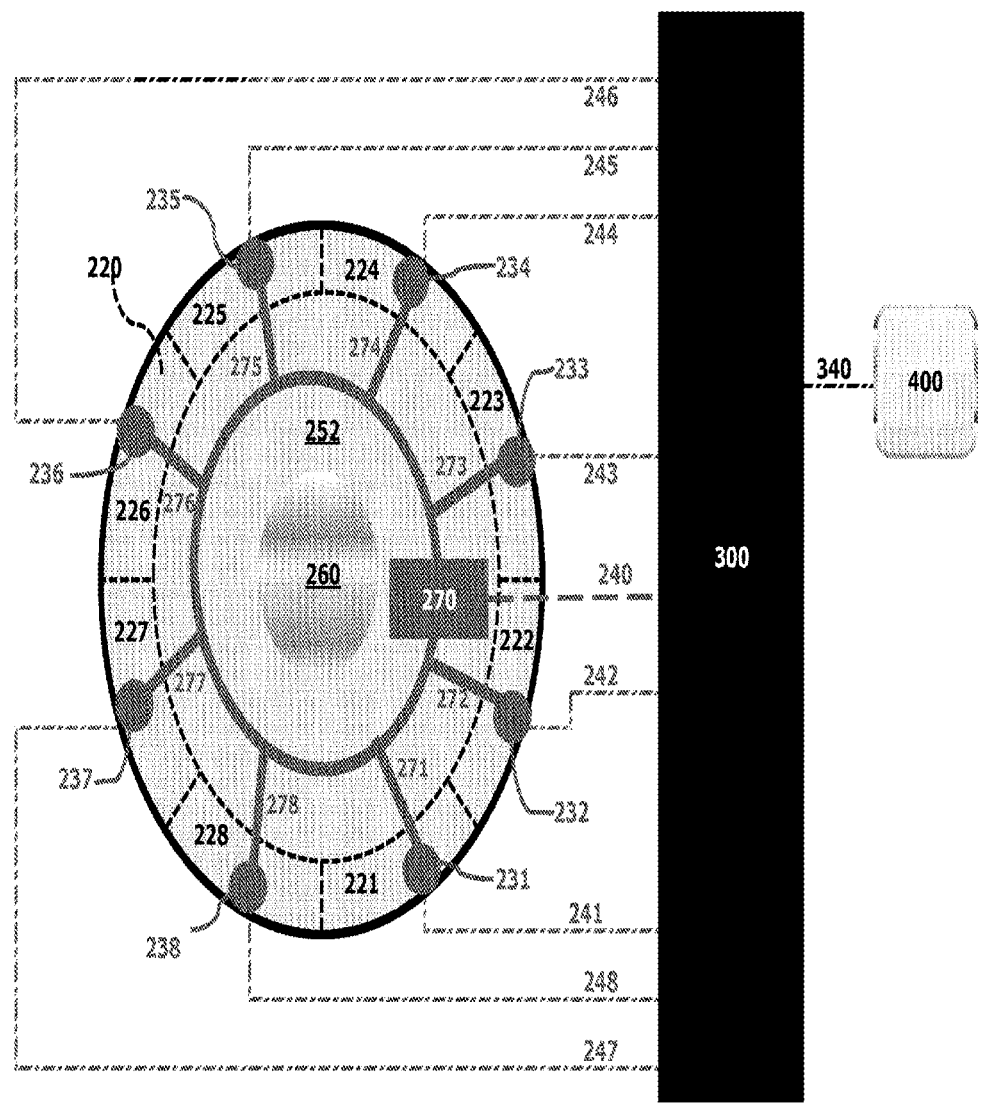
FIG. 2F is a diagrammatic illustration of a stability-assessing system including exemplary sensors in accordance with one aspect of the disclosed technology.

Additionally or alternatively, the sensors 231-238 can communicate with a platform-integral subprocessor 270 which in turn communicates with the processor 300 via communication course 240. (FIGS. 2E-2F.) Sensor-to-subprocessor communication is can be established via communication lines 271-278. The subprocessor 270 communicates with the processor 300 via communication course 240. The communication lines 271-278 can be used instead of the lines 241-248 or in addition thereto. The subprocessor 270 can (or cannot) also communicate with the processor via communication course 240.

Figure 2G:
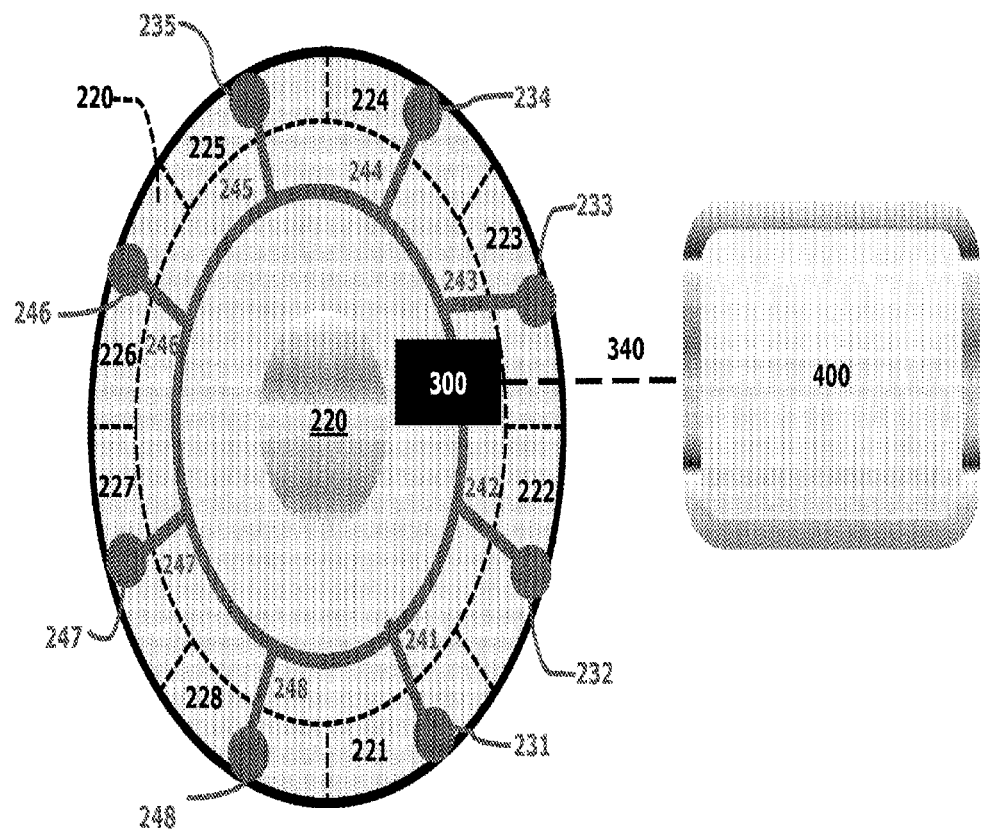
FIG. 2G is a diagrammatic illustration of a stability-assessing system including exemplary sensors in accordance with one aspect of the disclosed technology.
Figure 2H:
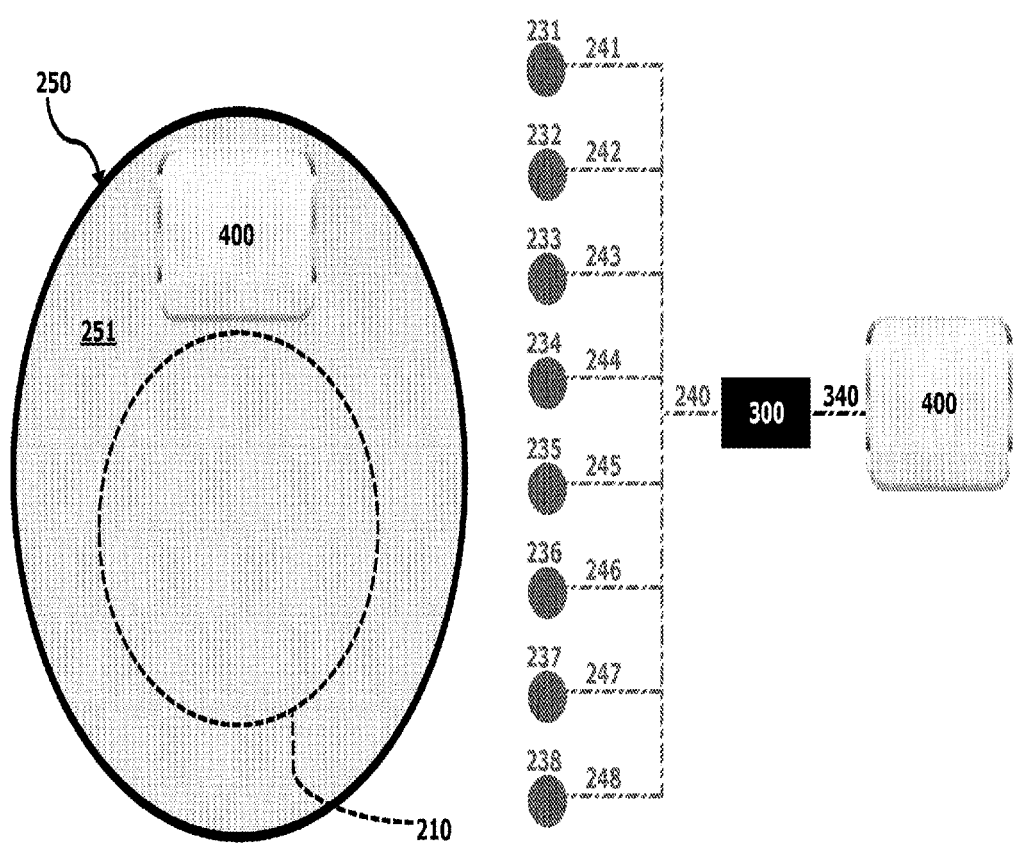
FIG. 2H is a diagrammatic illustration of a stability-assessing system including exemplary sensors in accordance with one aspect of the disclosed technology.
Figure 2I:
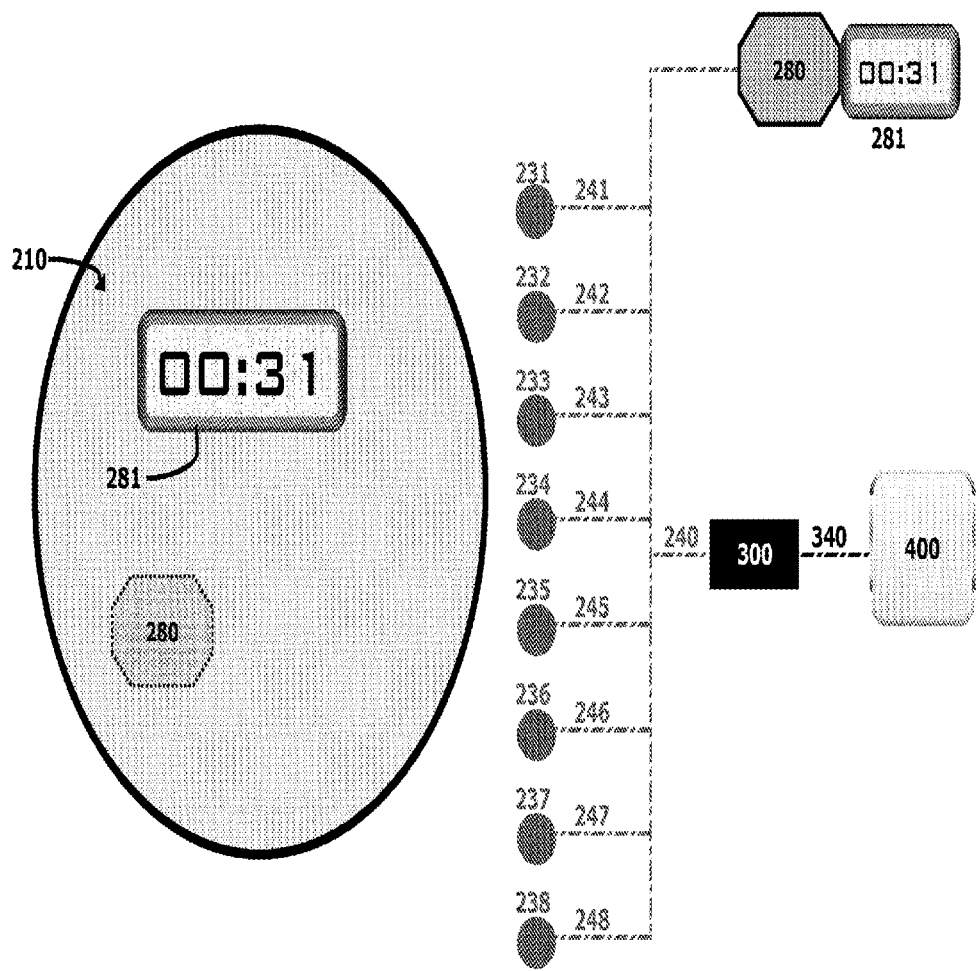
FIG. 2I is a diagrammatic illustration of a stability-assessing system including exemplary sensors in accordance with one aspect of the disclosed technology.
Figure 2J:
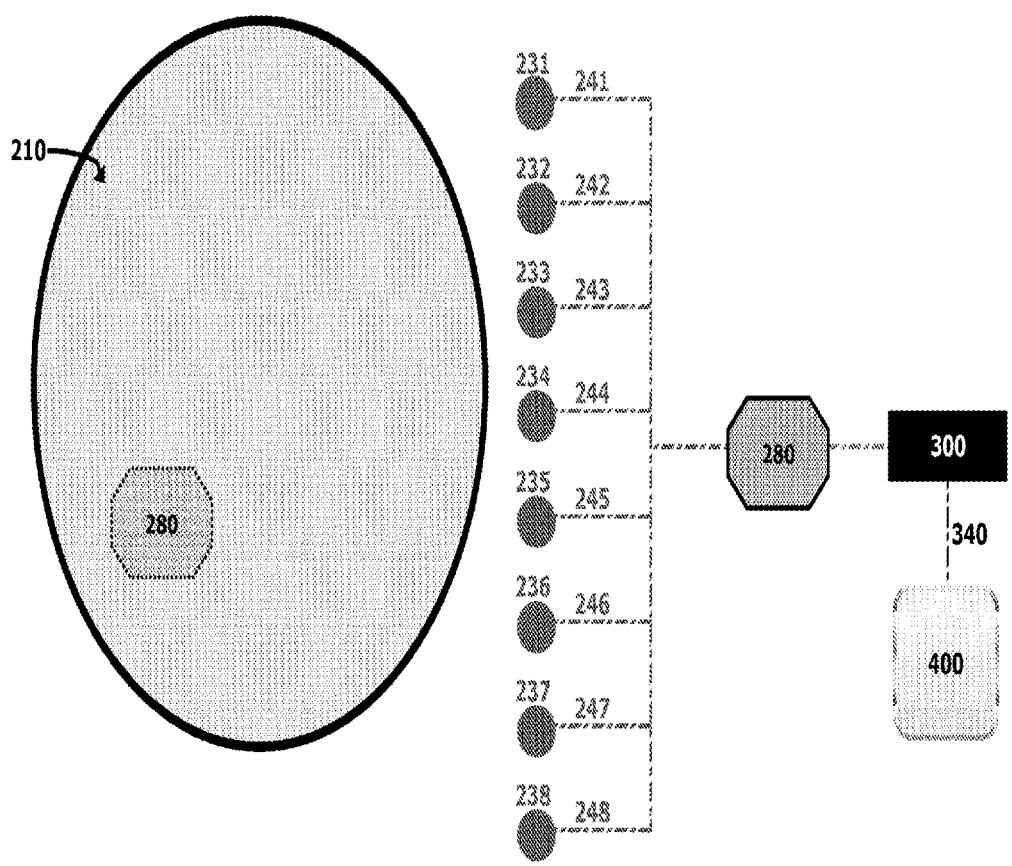
FIG. 2J is a diagrammatic illustration of a stability-assessing system including exemplary sensors in accordance with one aspect of the disclosed technology.

The processor 300 can be incorporated into the platform 200 rather than being remote therefrom. (FIGS. 2G-2H.) If so, the sensors 231-238 can communicate with the processor 300 via sensor—processor communication lines 241-248. The processor 300 can communicate with a platform-remote the display device 400 via the communication course 340. Or the display device 400 can be likewise incorporated into the platform 200.

Figure 2K:
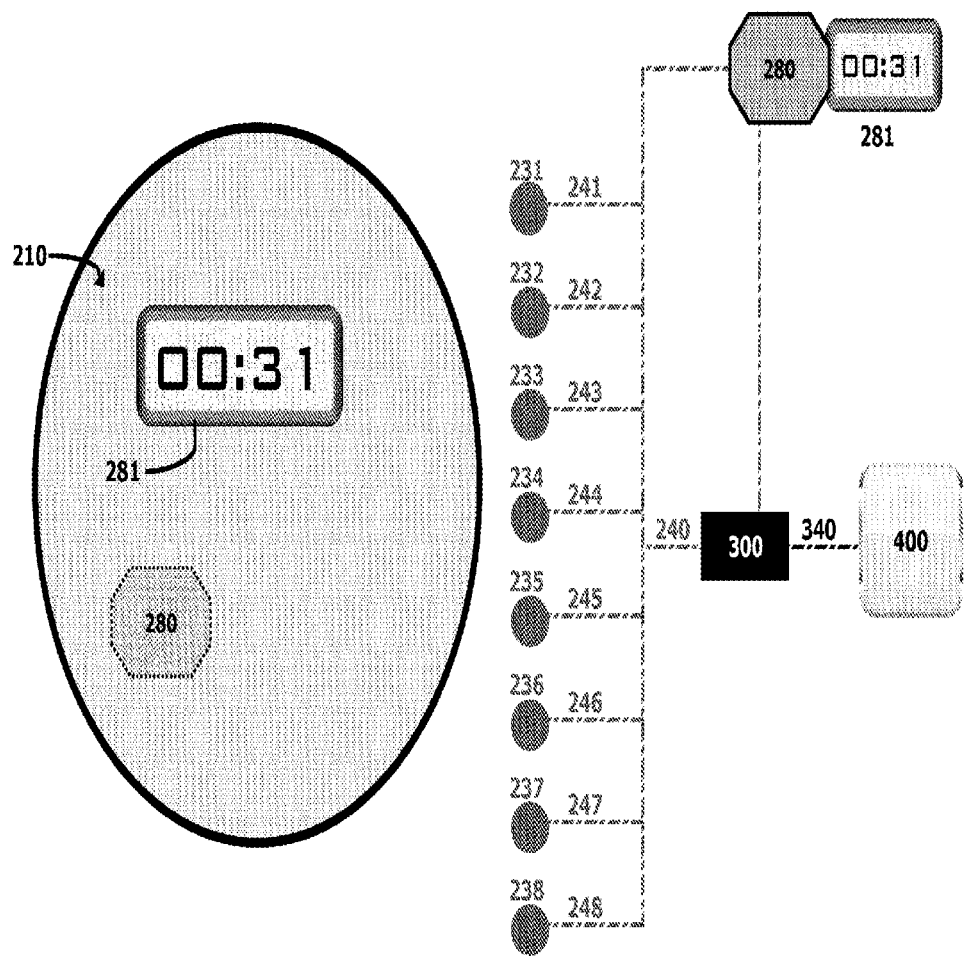
FIG. 2K is a diagrammatic illustration of a stability-assessing system including exemplary sensors in accordance with one aspect of the disclosed technology.

The platform 200 can additionally or alternatively incorporate a timing appliance 280. (FIGS. 21-2K.) The timing appliance 280 can be used to calculate pertinent time periods based on input from the sensing configuration 230. The pertinent-time-period information can be presented on a panel 281 mounted on the platform 200 for perusal by the person 110. Additionally or alternatively, the pertinent-time-period information can be conveyed to the processor 300 via the communication course 240. The timing appliance 280 can instead be incorporated into the platform-integral subprocessor 270 and/or the processor 300.

For example, the timing appliance 280 can be used to measure the total duration of an assessment time period (ttotal). The timing appliance 280 can be used to determine a time summation (tbalance) indicative of the sum of time intervals during which the person 110 is balanced on the stage 210. The time summations computed by the appliance 280 can be based on the zones collectively and/or individually.

The processor or controller 300 can comprise any computer or combination of computing device, hardware, firmware or the like capable of receiving balance statistics from the platform 200, converting such received data into meaningful information, and conveying the meaningful information to the display 400. Temporary and/or long term storage abilities can also be included.

Figure 3A:
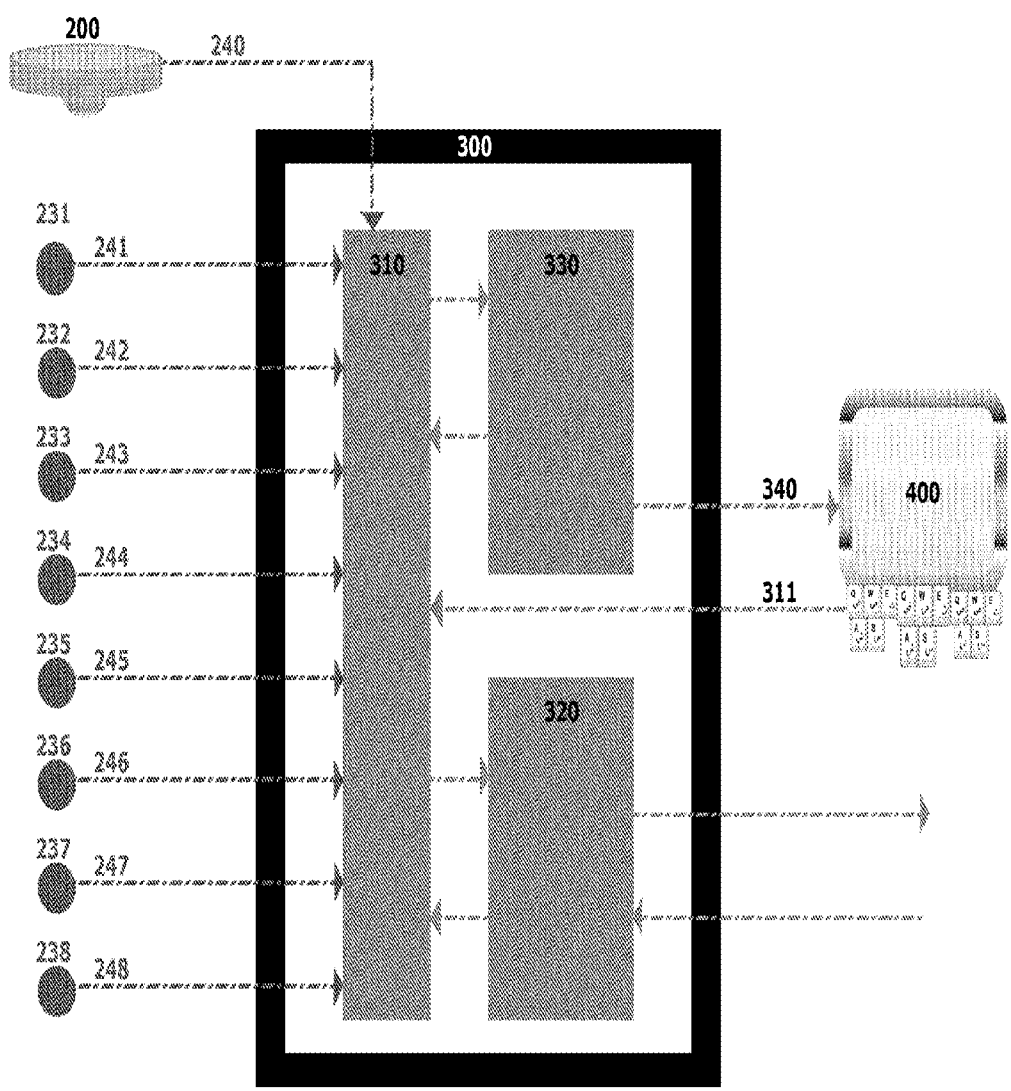
FIG. 3A is a diagrammatic illustration of a stability-assessing system in accordance with one aspect of the disclosed technology.
Figure 3B:
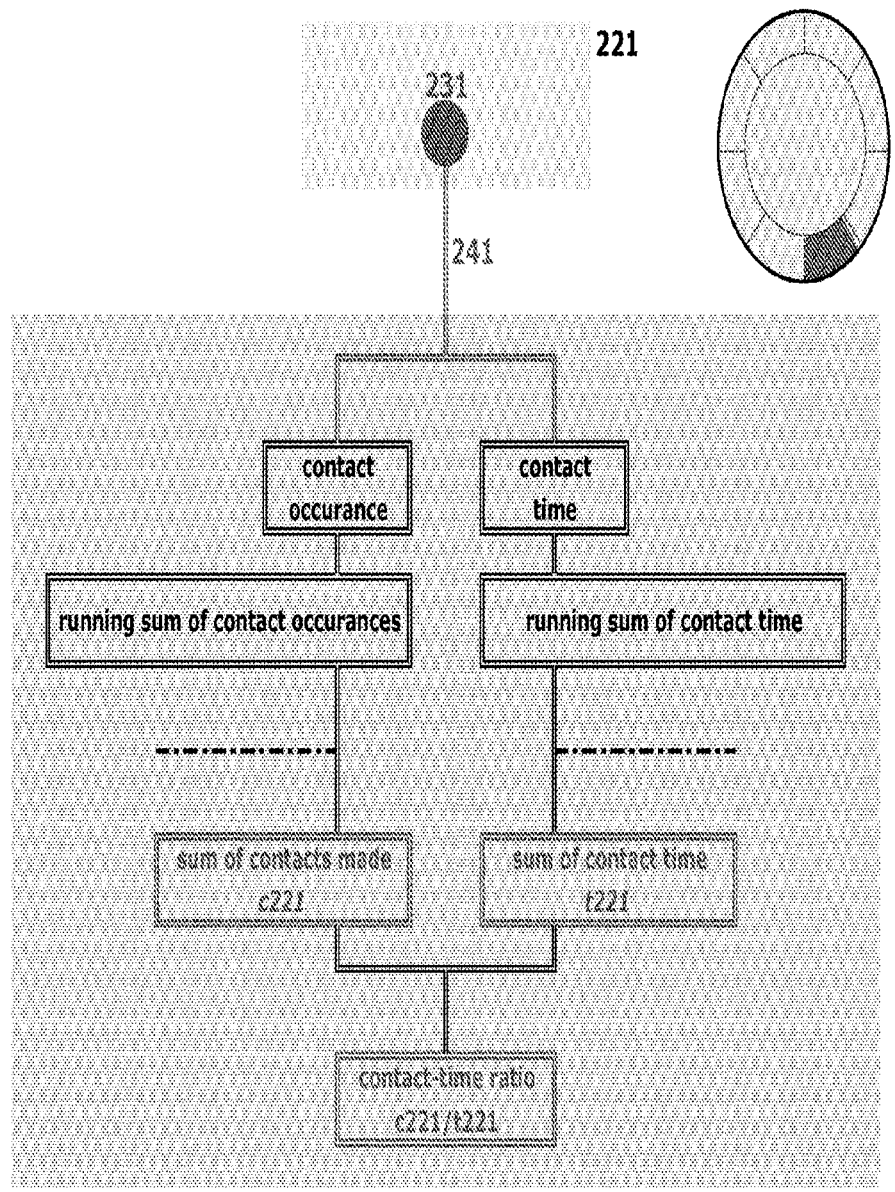
FIG. 3B is a flow diagram and diagrammatic illustration of an operational method making use of the stability-assessing system in accordance with one aspect of the disclosed technology.
Figure 3C:
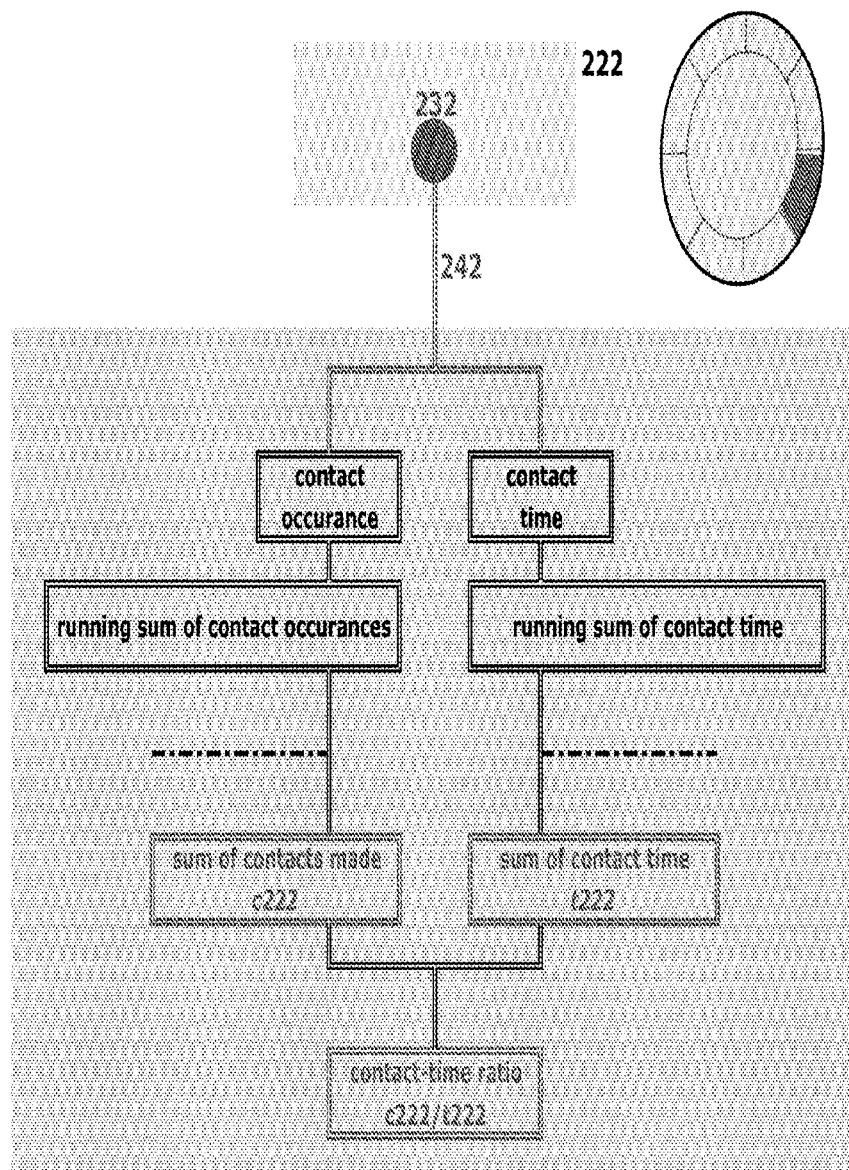
FIG. 3C is a flow diagram and diagrammatic illustration of an operational method making use of the stability-assessing system in accordance with one aspect of the disclosed technology.
Figure 3D:
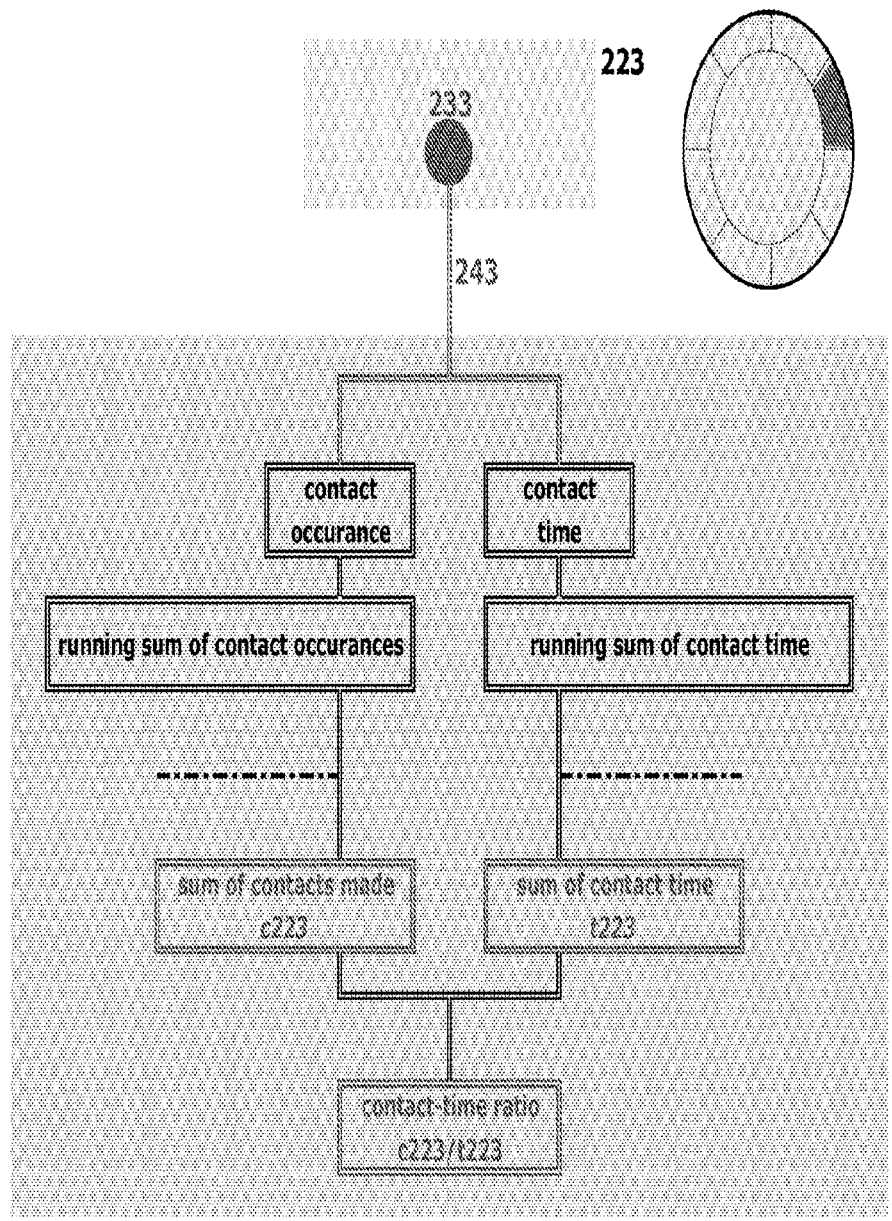
FIG. 3D is a flow diagram and diagrammatic illustration of an operational method making use of the stability-assessing system in accordance with one aspect of the disclosed technology.
Figure 3E:
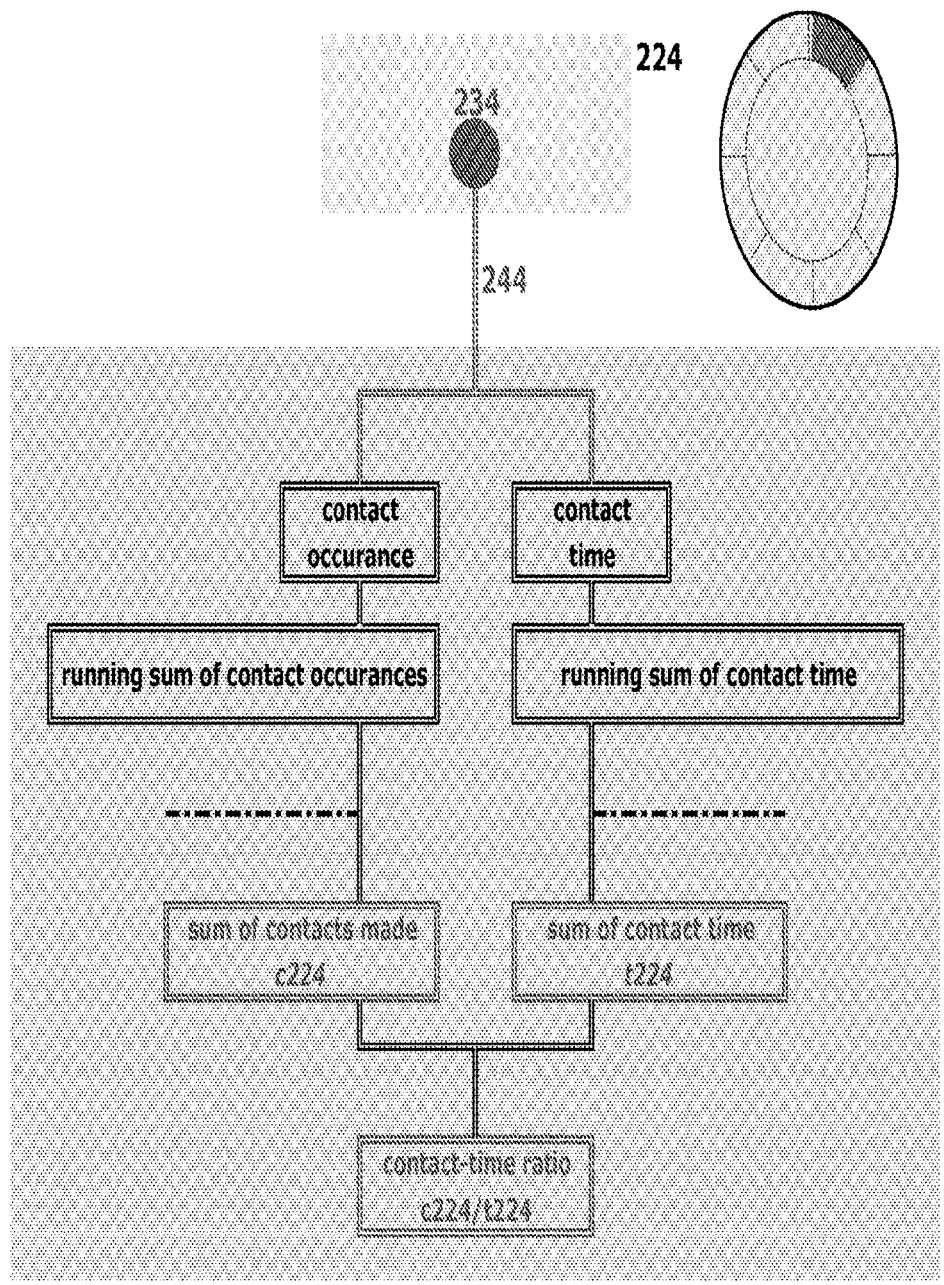
FIG. 3E is a flow diagram and diagrammatic illustration of an operational method making use of the stability-assessing system in accordance with one aspect of the disclosed technology.
Figure 3F:
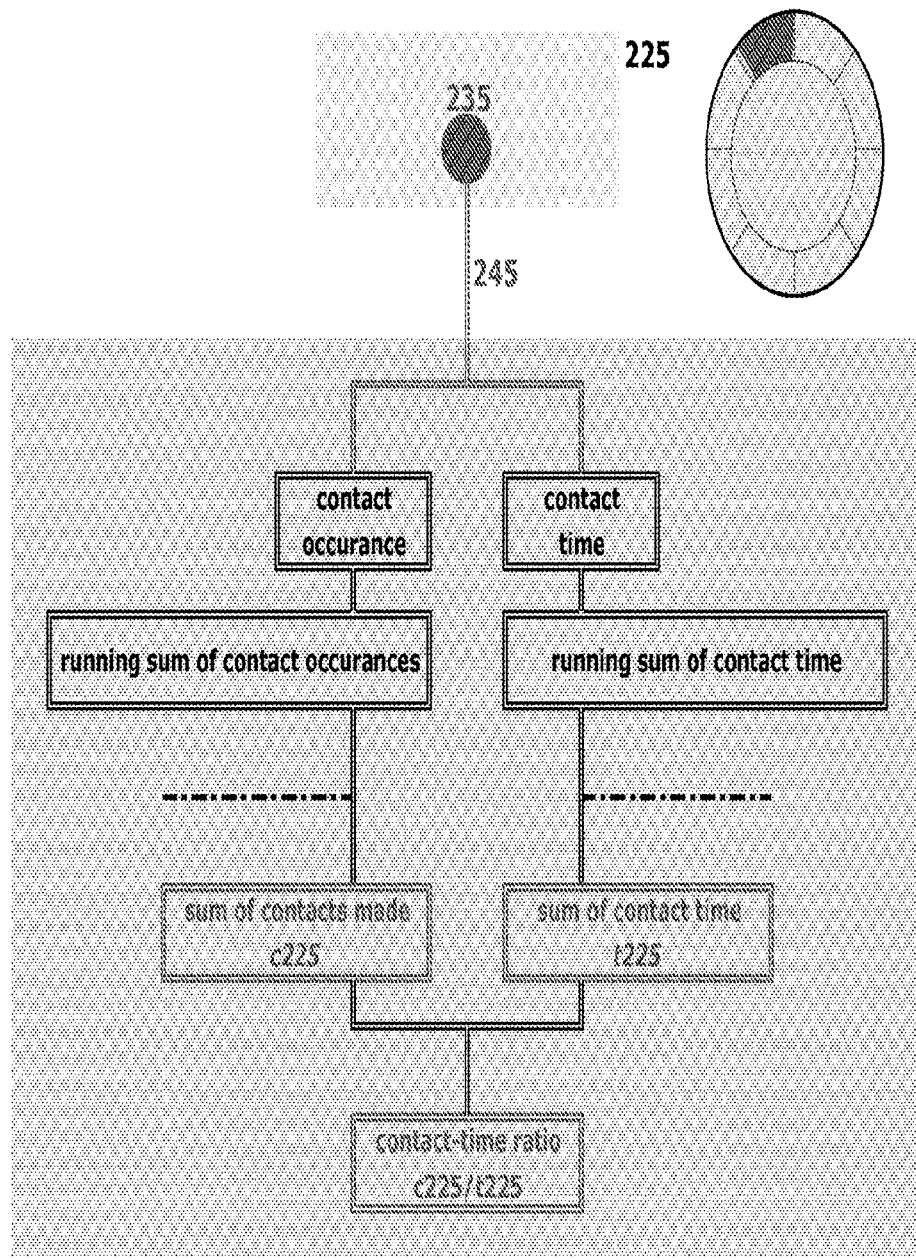
FIG. 3F is a flow diagram and diagrammatic illustration of an operational method making use of the stability-assessing system in accordance with one aspect of the disclosed technology.
Figure 3G:
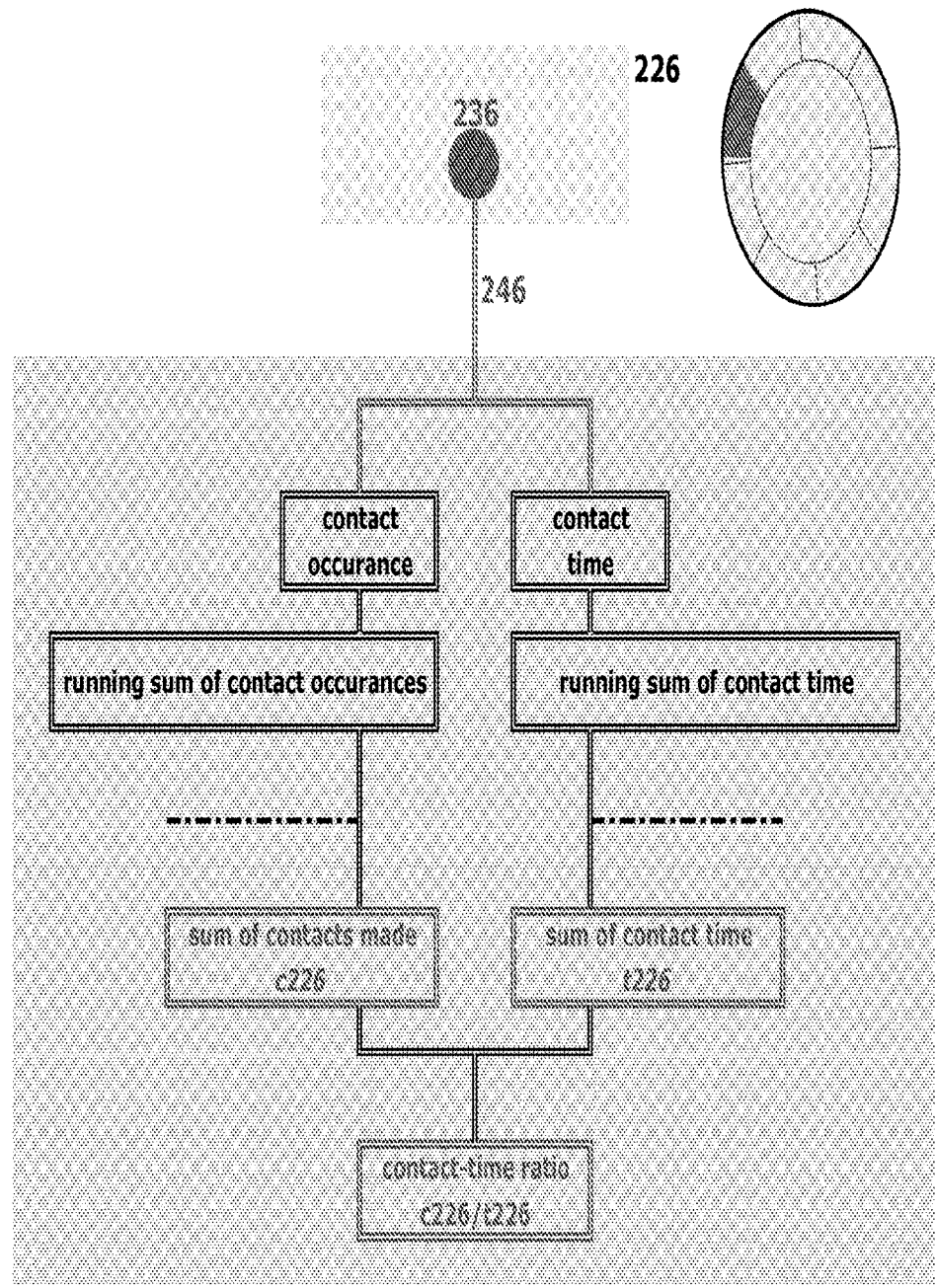
FIG. 3G is a flow diagram and diagrammatic illustration of an operational method making use of the stability-assessing system in accordance with one aspect of the disclosed technology.
Figure 3H:
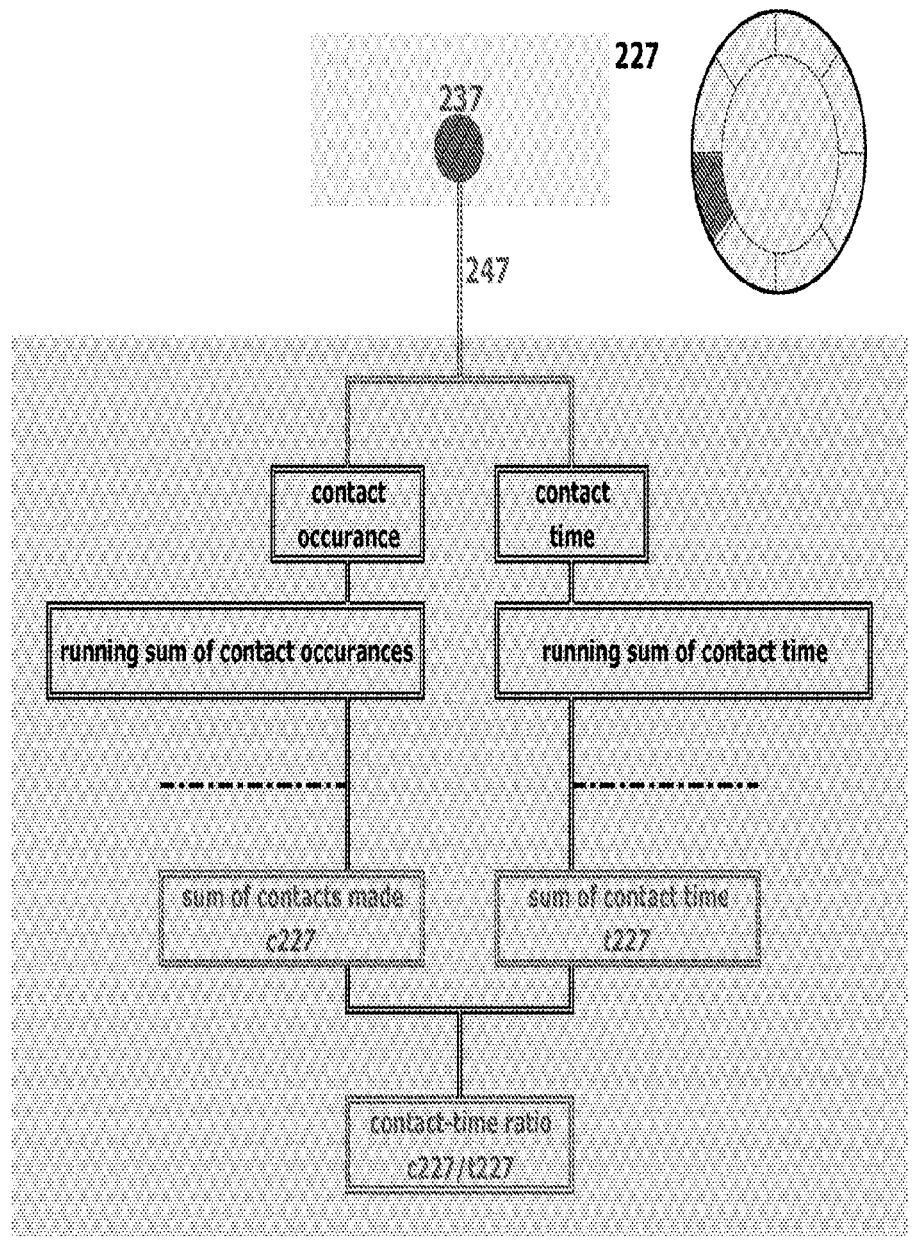
FIG. 3H is a flow diagram and diagrammatic illustration of an operational method making use of the stability-assessing system in accordance with one aspect of the disclosed technology.
Figure 3I:
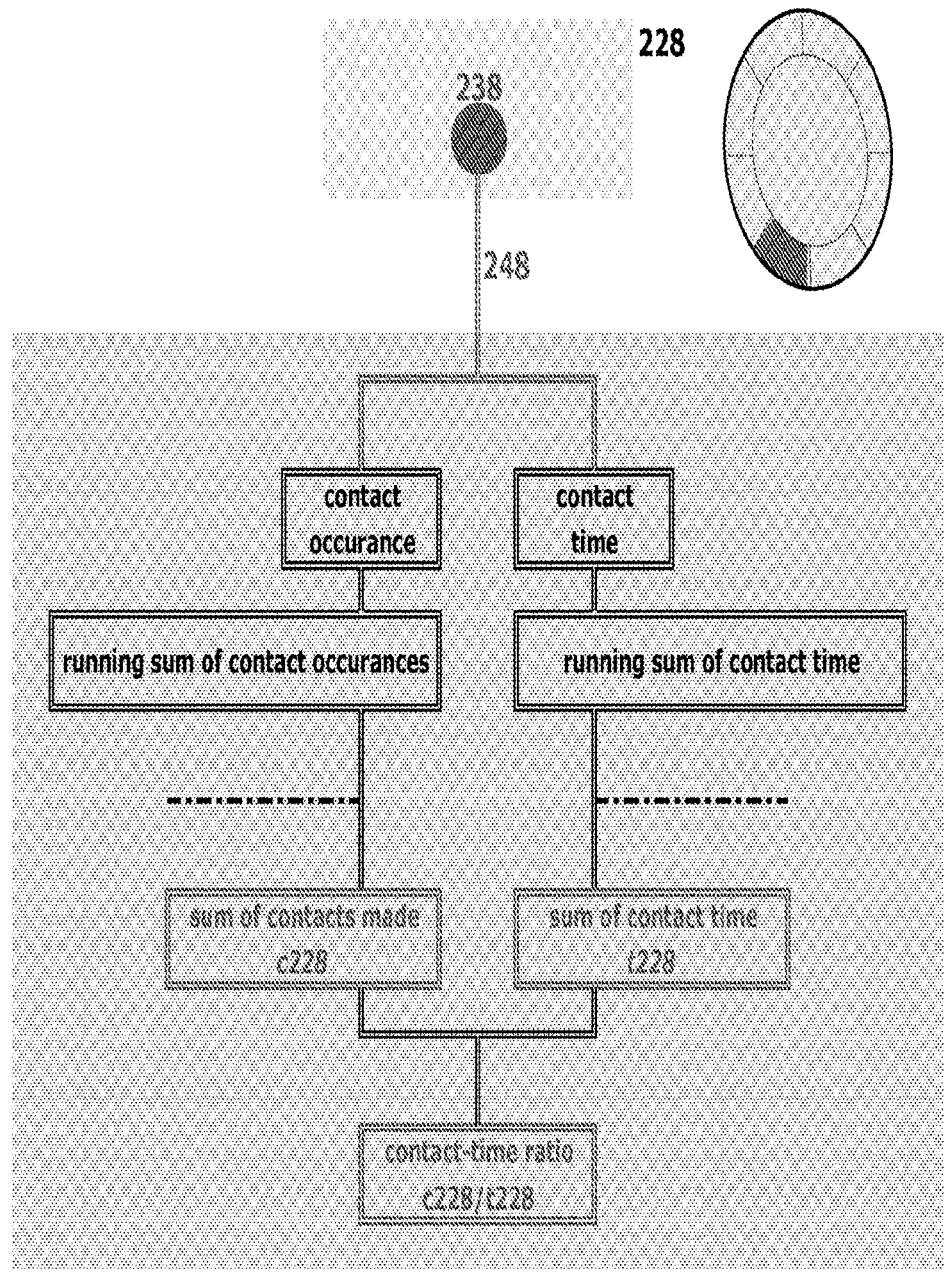
FIG. 3I is a flow diagram and diagrammatic illustration of an operational method making use of the stability-assessing system in accordance with one aspect of the disclosed technology.
Figure 3J:
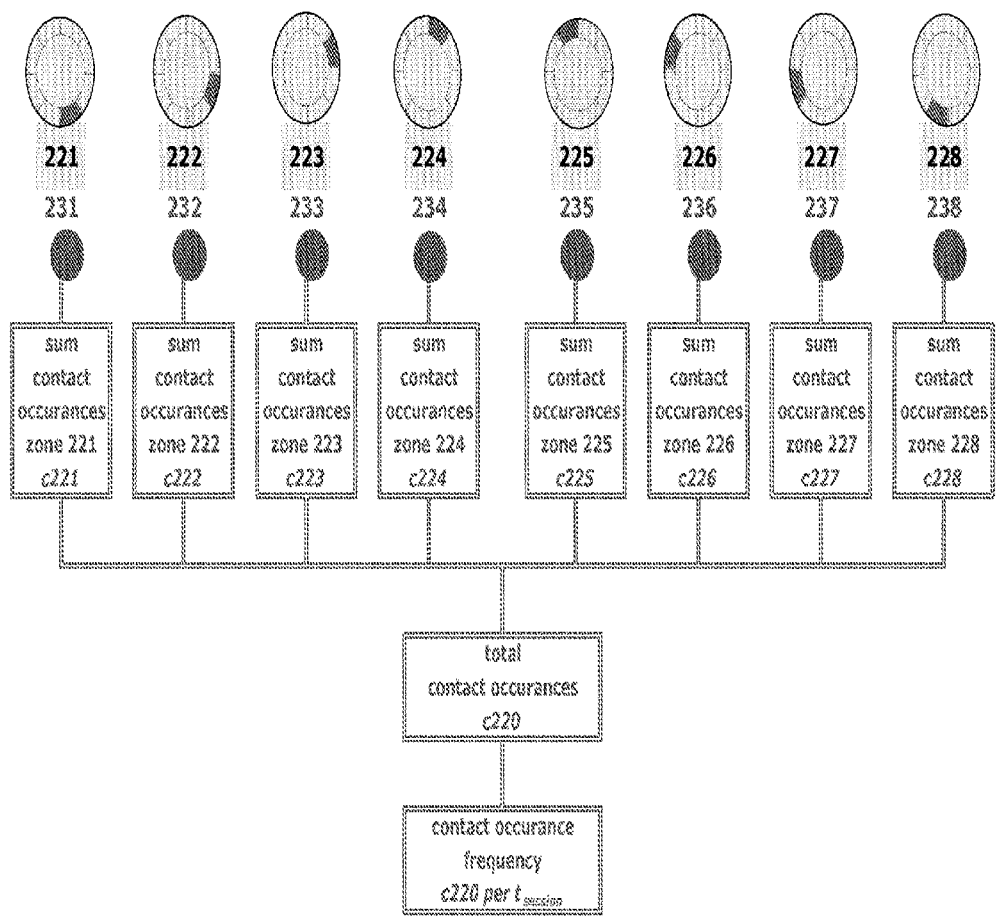
FIG. 3J is a flow diagram and diagrammatic illustration of an operational method making use of the stability-assessing system in accordance with one aspect of the disclosed technology.
Figure 3K:
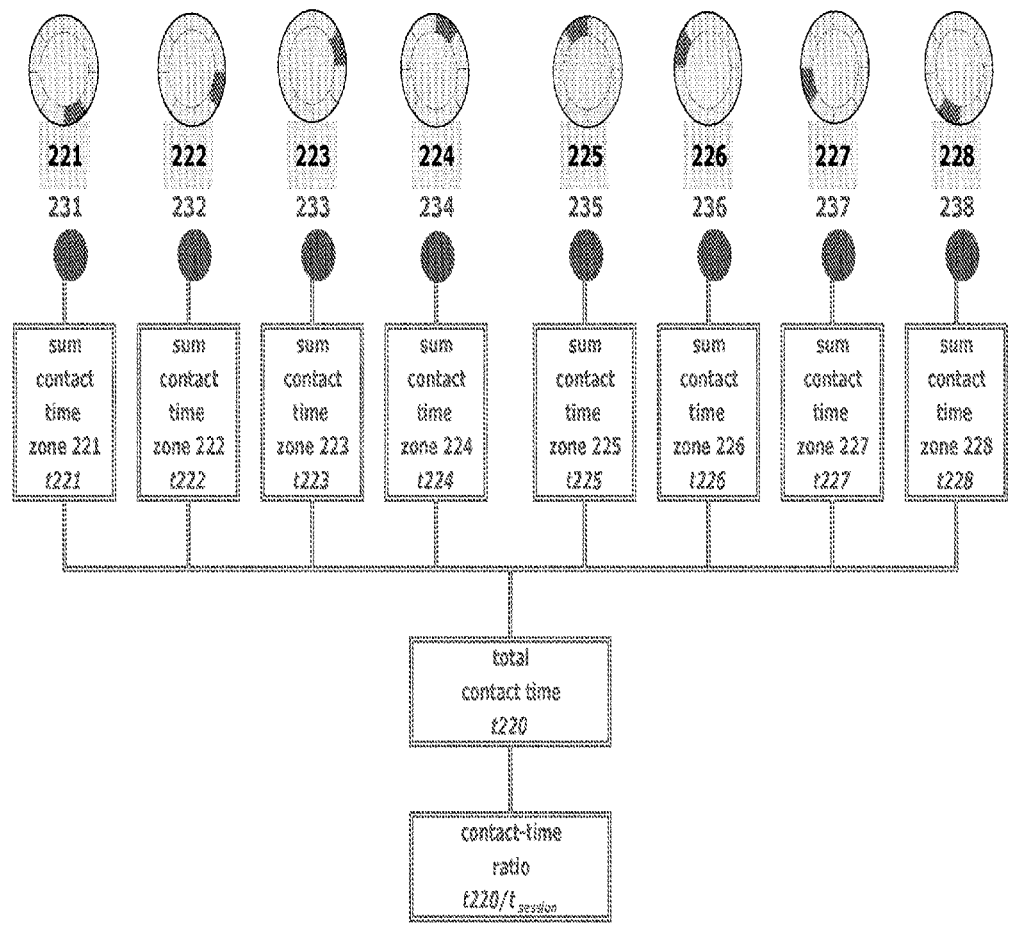
FIG. 3K is a flow diagram and diagrammatic illustration of an operational method making use of the stability-assessing system in accordance with one aspect of the disclosed technology.
Figure 3L:
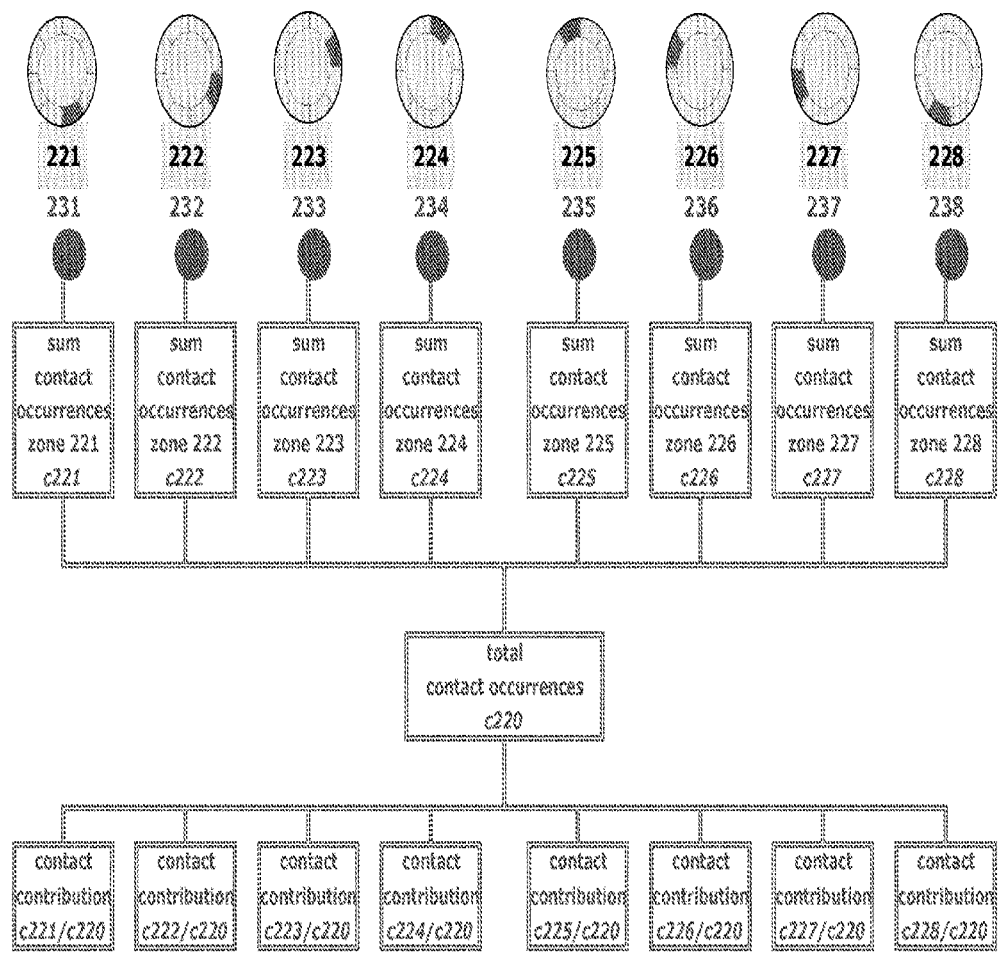
FIG. 3L is a flow diagram and diagrammatic illustration of an operational method making use of the stability-assessing system in accordance with one aspect of the disclosed technology.
Figure 3M:
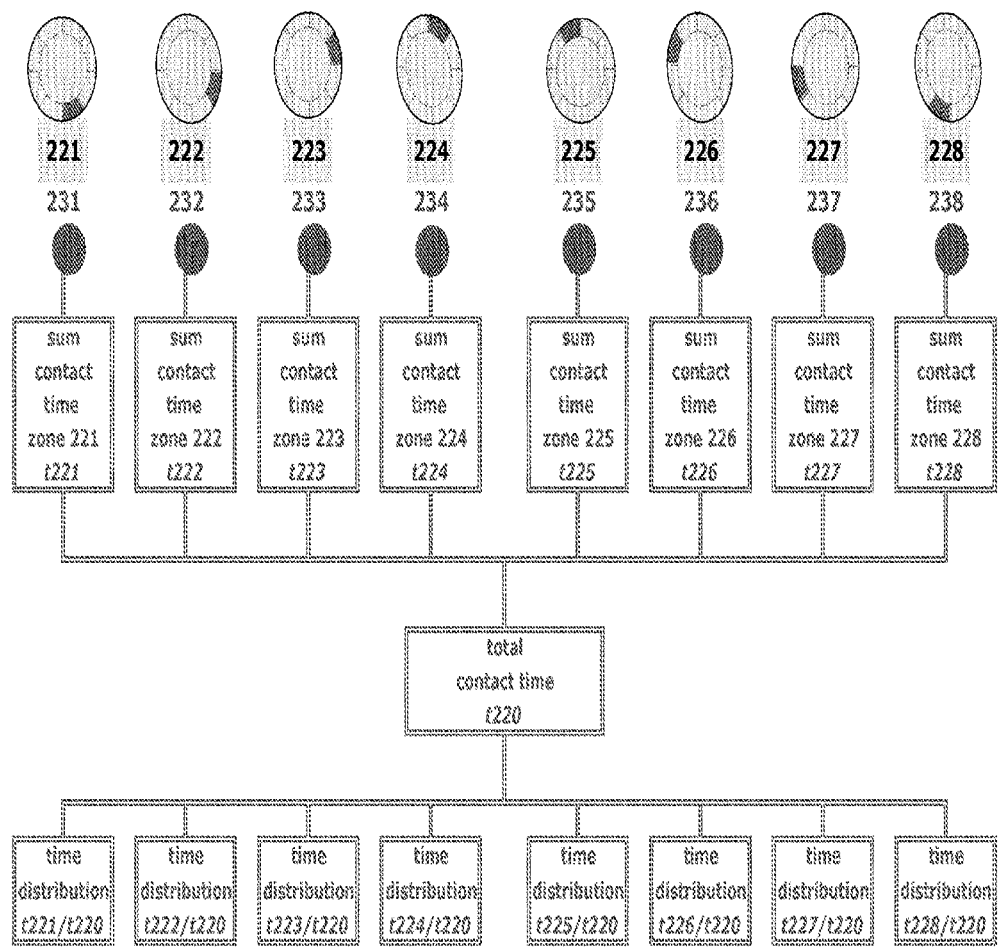
FIG. 3M is a flow diagram and diagrammatic illustration of an operational method making use of the stability-assessing system in accordance with one aspect of the disclosed technology.

The illustrated processor 300 comprises a processing unit 310, a memory 320, and an output interface 330. (FIG. 3A.) Generally, the processing unit 310 is the "brains" of the processor 300, the memory 320 serves as a data storage facility, and the interface 330 allows output to the display 400.

More particularly, for example, the processing unit 310 can receive balance statistics from the sensors 231-238 via, for example, communication lines 241-248. It can also receive balance statistics from other sources in the platform 200, such as the internal subprocessor 270 and/or the timing appliance 280. Other relevant input can be received by processing unit 310 via a communication course 311. This relevant information could include, for example, an identifier of the person (e.g., name and/or patient code), the date, assessment type, and/or other details.

The memory 320 can be used store, either temporarily or permanently, information received by the processing unit 310. The processing unit 310 can preferably pull stored information from the memory 320 when converting data into meaningful information. The memory 320 can also be supplied with information from outside records and/or it can be downloaded for safekeeping in remote storage sites.

The interface 330 can generate output images for visual viewing on the display 400. The output interface 330 can include, for example, cards or chips which enable accelerated rendering of information in graphical form. The interface 330 is operably coupled to the display 400 via the communication course 340, which can be wired or wireless.

The processing unit 310 can be programmed to convert sensor and other data received into meaningful information. For example, the processing unit 310 can calculate, based on input from each sensor 231-238, balance aspects particular to each zone 221-228. (FIGS. 2B-2I.) These aspects could include total occurrences of contacts ($c221$-$c228$) in each zone and the total time of such contacts ($t221$-$228$) in each zone. Zone-particular aspects can be used, for example, to create markers representative of balance performance. (FIGS. 2H-2M.) These markers could entail, for example, contact occurrence frequency ($c220$ per tsession), contact-time ratio ($t220$/tsession), zone-by-zone contact occurrence contributions ($c221/c220$-$c228/c220$), and zone-by-zone contact time distribution ($t221/t220$-$t228/t220$).

The display 400 can comprise any piece or combination of equipment capable of visual presentation. This equipment could comprise, for example, a laptop computer, a tablet, a mobile communications device, or other permanent or portable accessories.

The markers created by the processor 300 can be presented in graphical form on the display 400 for easy analysis. The graphs can be linear plots, column or row plots, and/or radial plots. A single set of data can be presented on the display 400 to evaluate current balance characteristics. If historical data is available (e.g., it is stored in the memory 320) a side-by-side or overlay diagram can be presented.

Figure 4A:
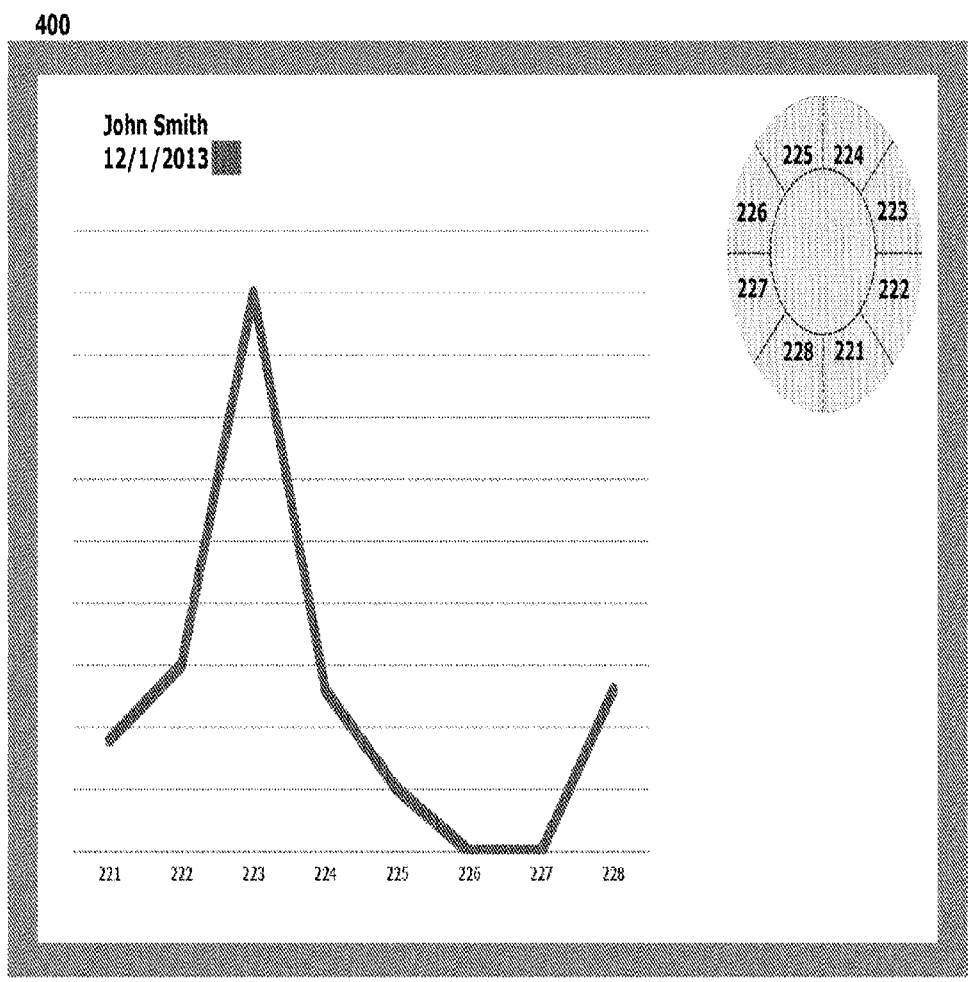
FIG. 4A is an exemplary visual representation of information collected using a stability-assessing system in accordance with one aspect of the disclosed technology.
Figure 4B:
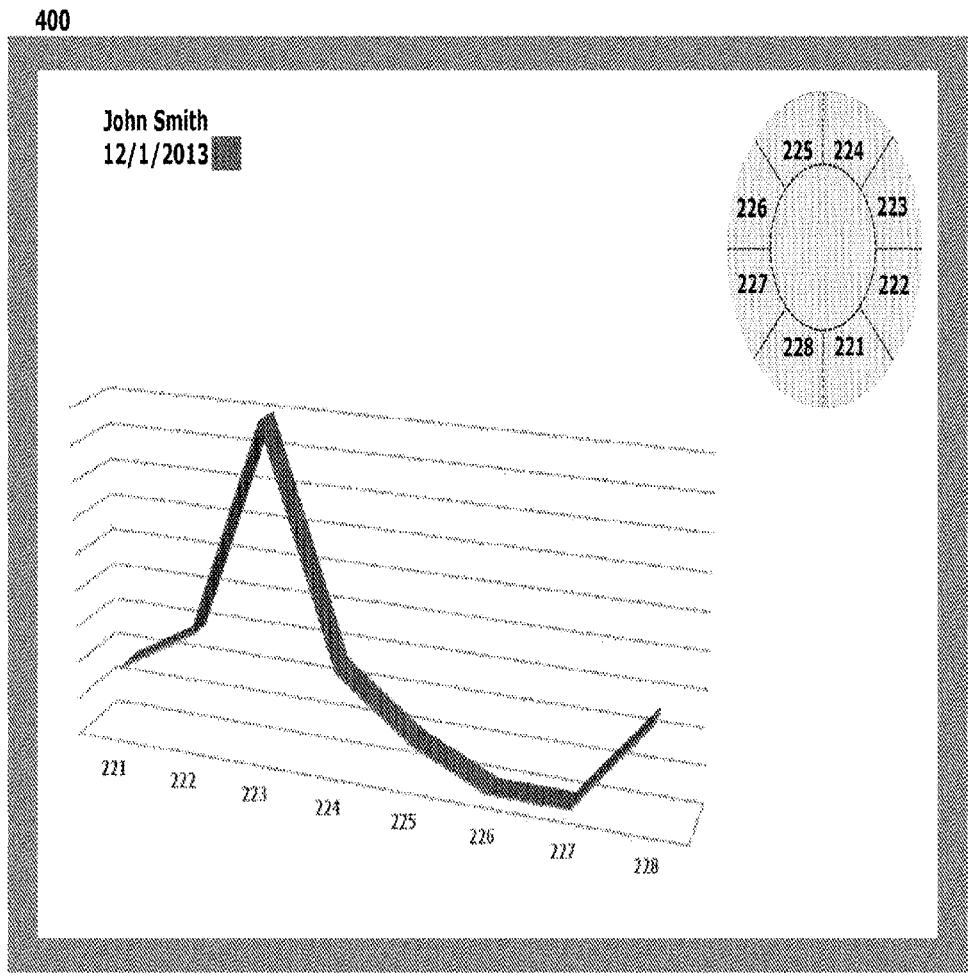
FIG. 4B is an exemplary visual representation of information collected using a stability-assessing system in accordance with one aspect of the disclosed technology.
Figure 4C:
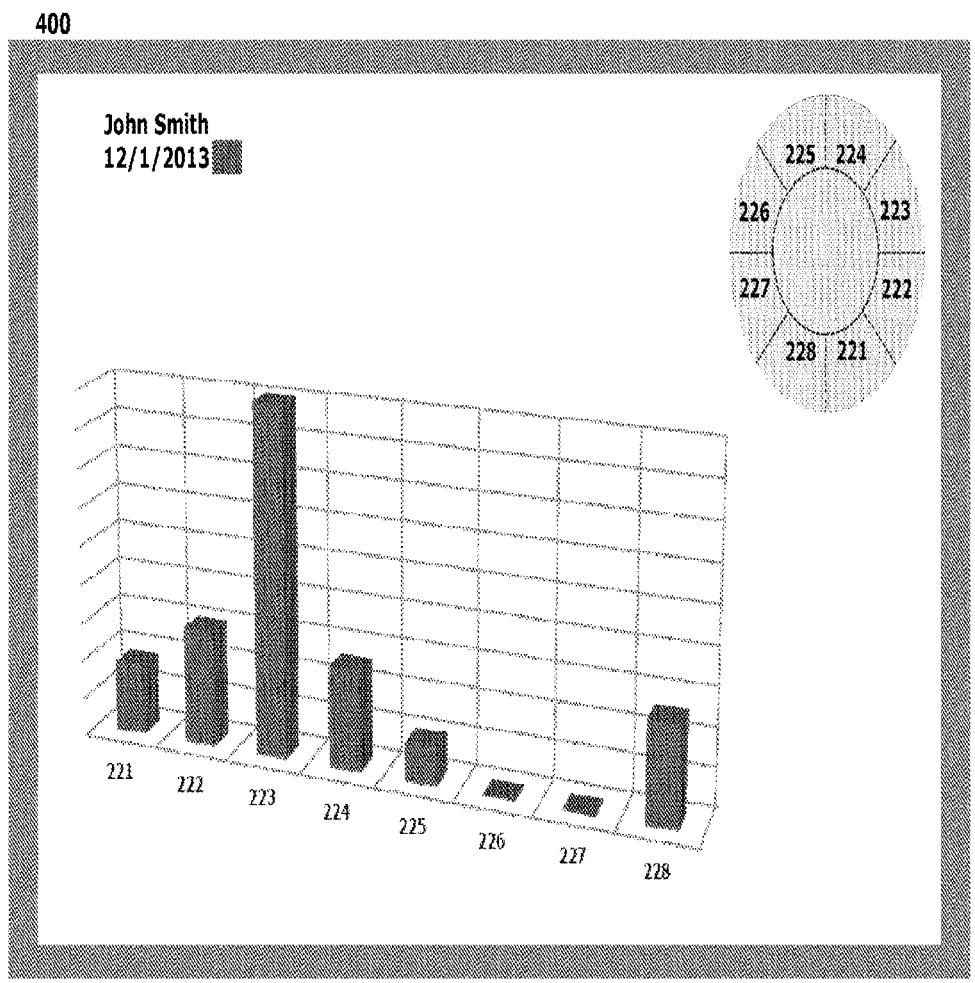
FIG. 4C is an exemplary visual representation of information collected using a stability-assessing system in accordance with one aspect of the disclosed technology.
Figure 4D:
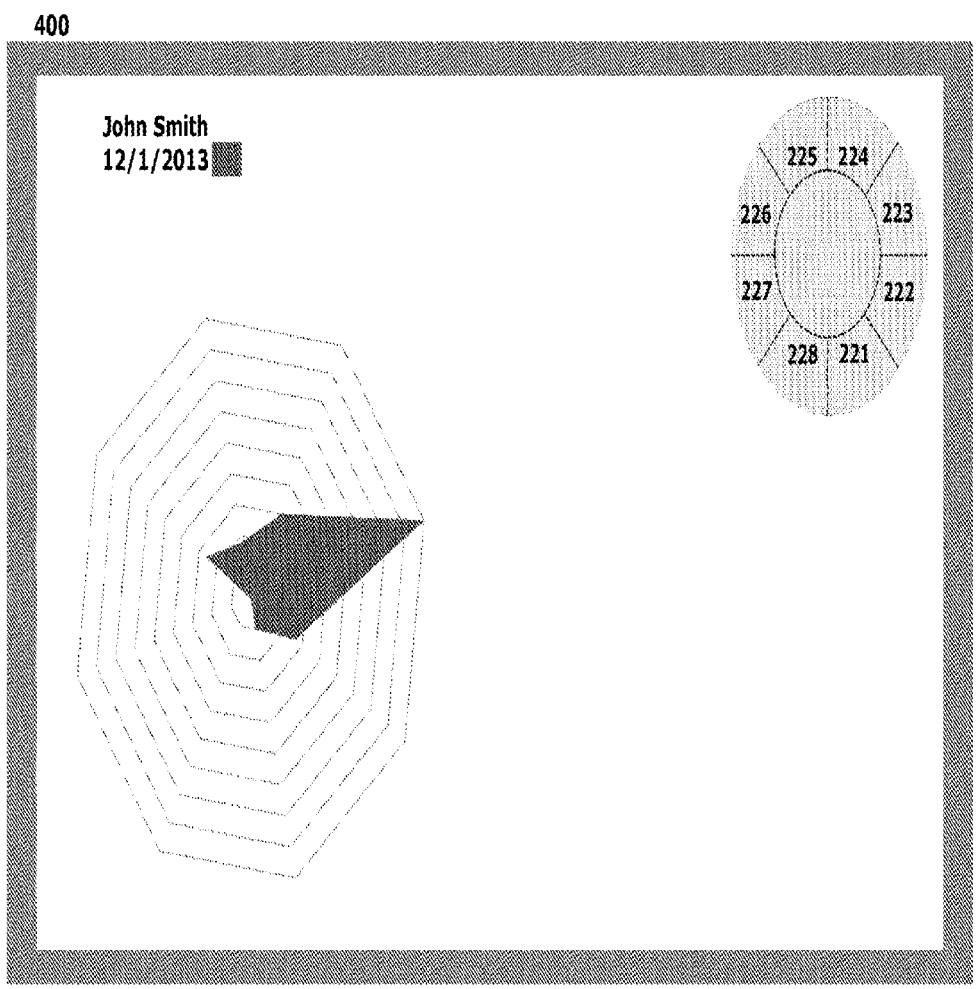
FIG. 4D is an exemplary visual representation of information collected using a stability-assessing system in accordance with one aspect of the disclosed technology.

It will be appreciated that the data and/or information collected using the stability-assessing device described above can be presented to a user (e.g., a patient, a physician, a therapist or the like) on display 400 in a number of ways without departing from the scope of the disclosed technology. For example, FIG. 4A illustrates an exemplary visual or graphical representation of data collected for a hypothetical patient in the form of a linear plot. FIG. 4C provides an exemplary bar graph showing stability data collected for a hypothetical patient in accordance with one aspect of the disclosed technology. FIG. 4D shows an exemplary visual representation of similar data collected for a hypothetical patient in the form of a radial plot.

Figure 4E:
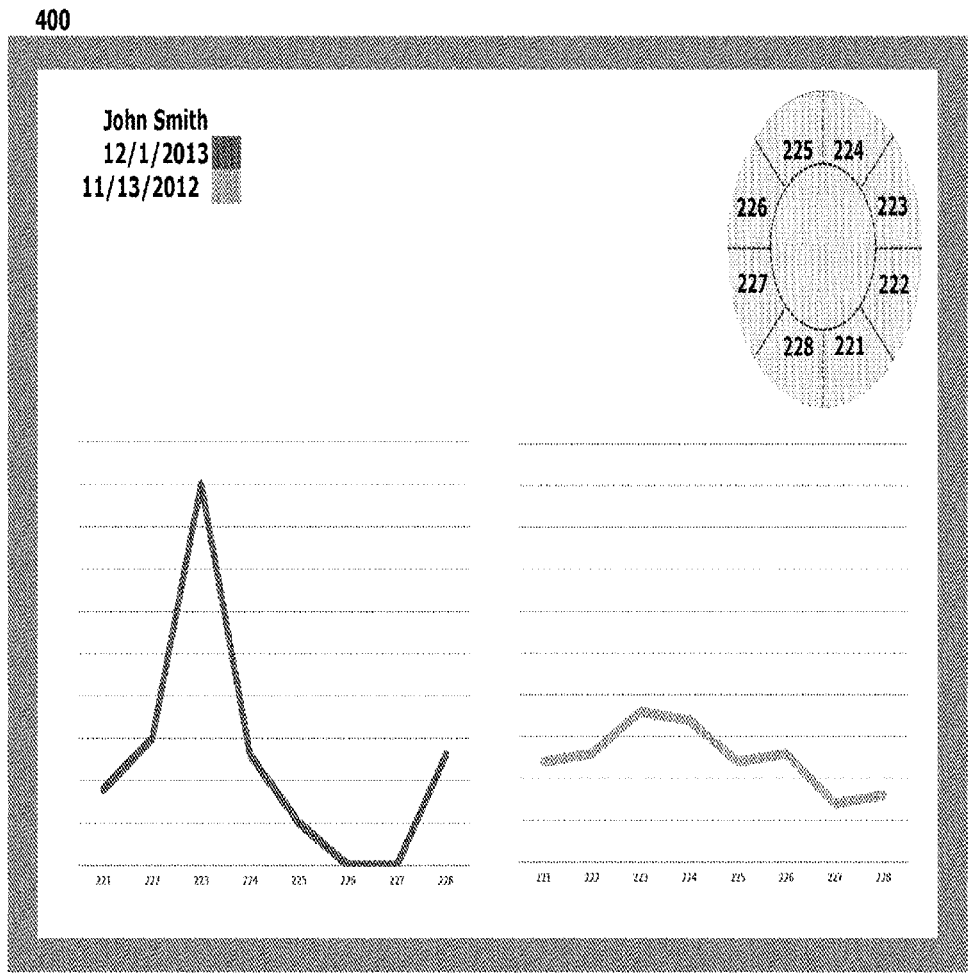
FIG. 4E is an exemplary visual representation of information collected using a stability-assessing system in accordance with one aspect of the disclosed technology.
Figure 4F:
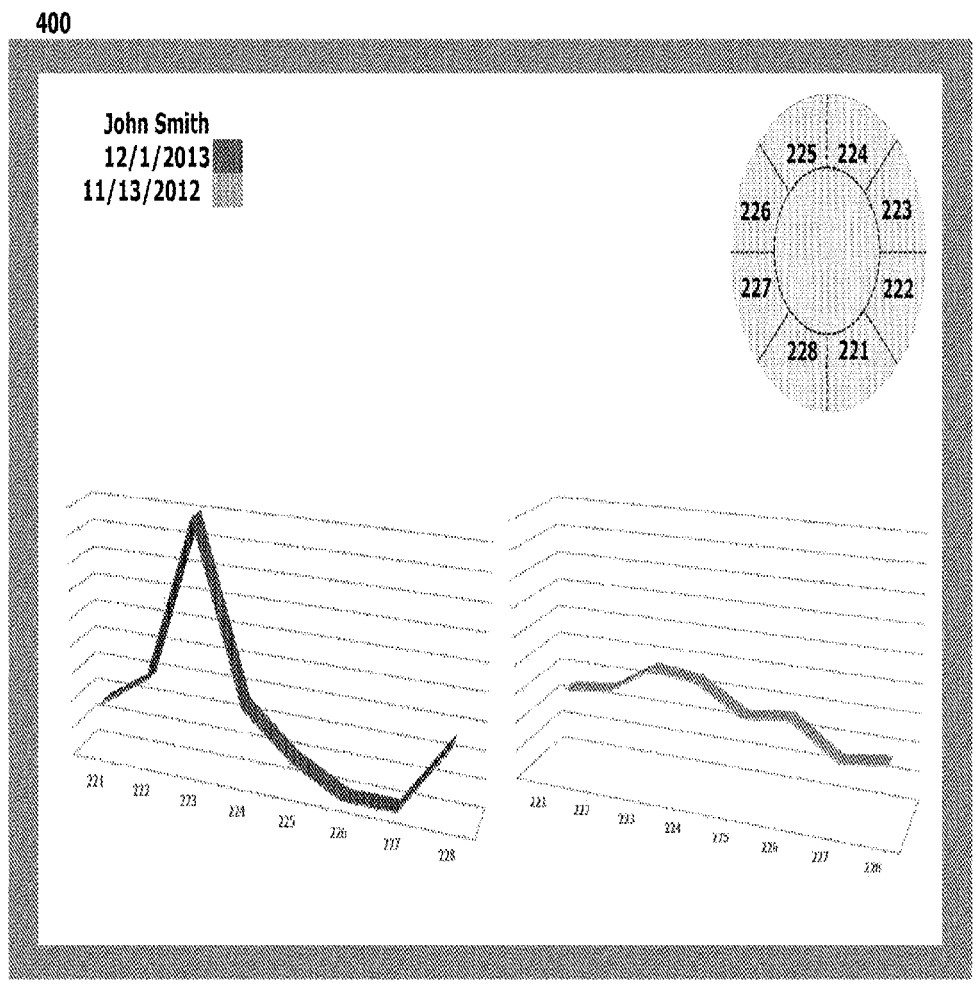
FIG. 4F is an exemplary visual representation of information collected using a stability-assessing system in accordance with one aspect of the disclosed technology.
Figure 4G:
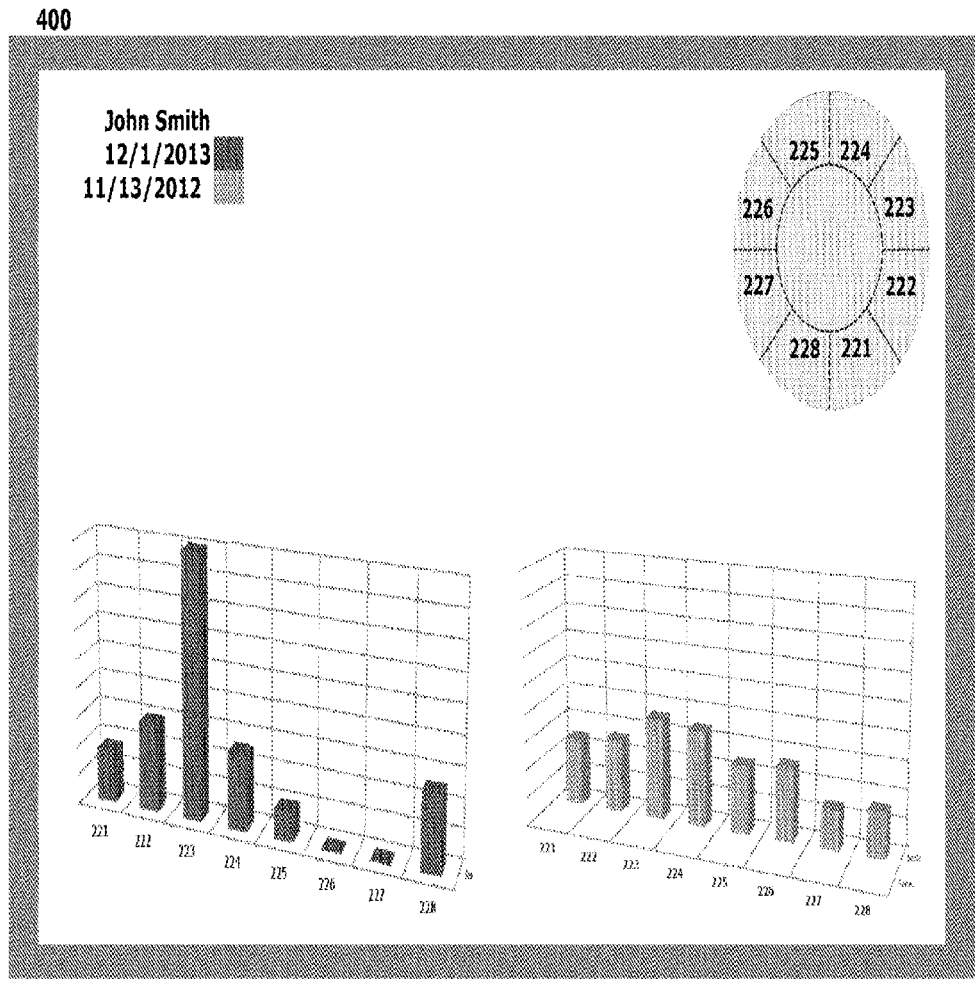
FIG. 4G is an exemplary visual representation of information collected using a stability-assessing system in accordance with one aspect of the disclosed technology.
Figure 4H:
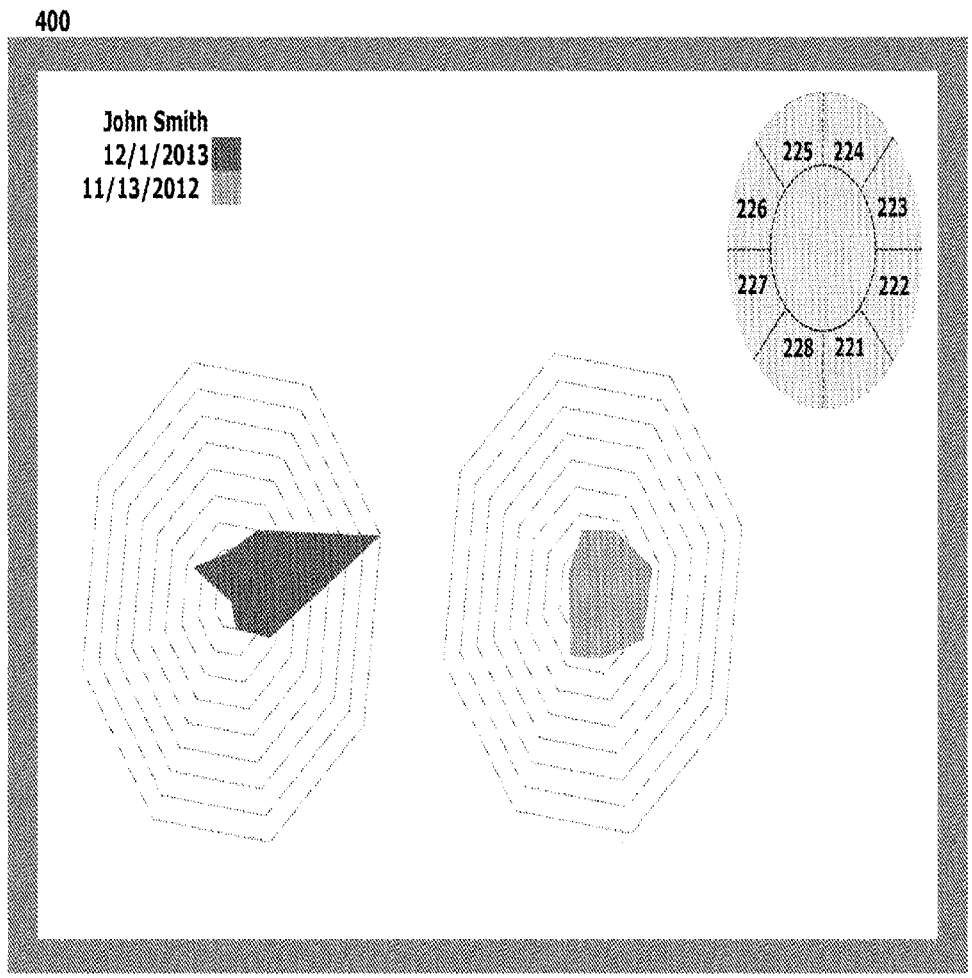
FIG. 4H is an exemplary visual representation of information collected using a stability-assessing system in accordance with one aspect of the disclosed technology.
Figure 4I:
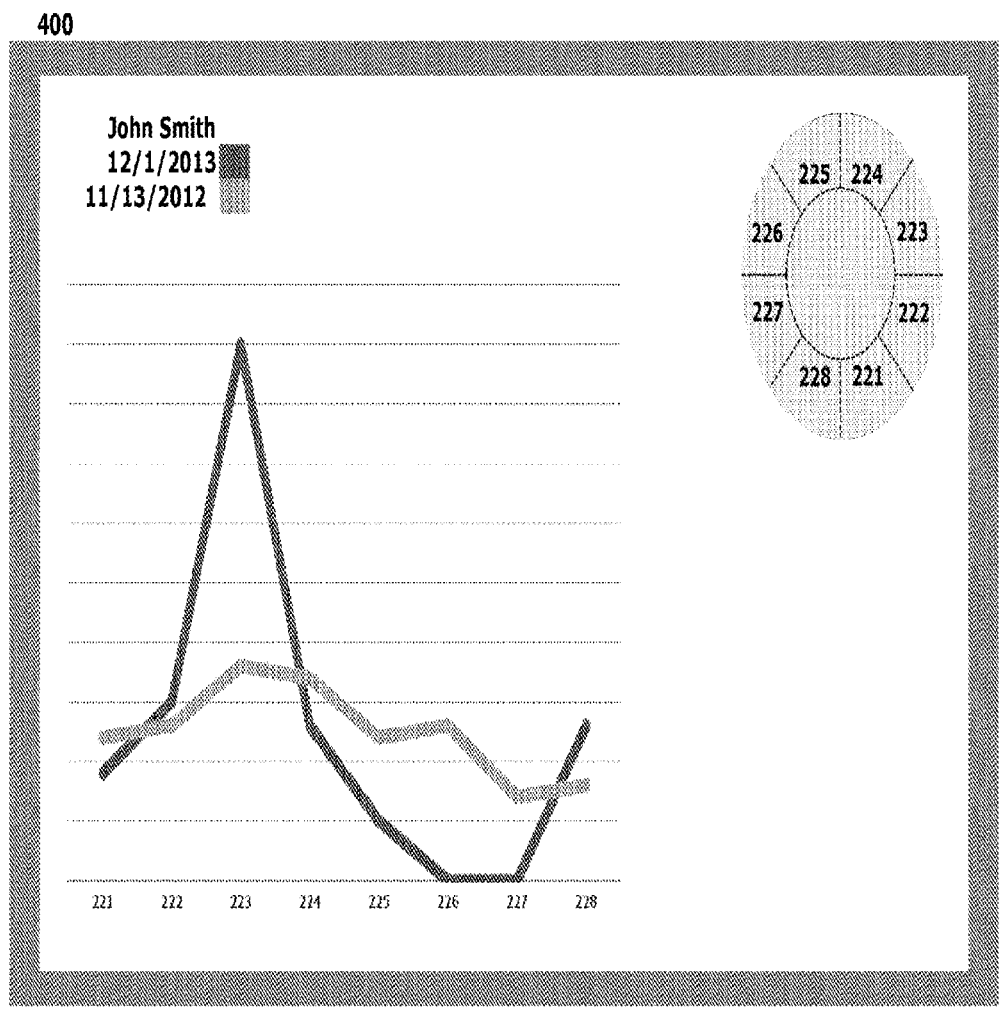
FIG. 4I is an exemplary visual representation of information collected using a stability-assessing system in accordance with one aspect of the disclosed technology.
Figure 4J:
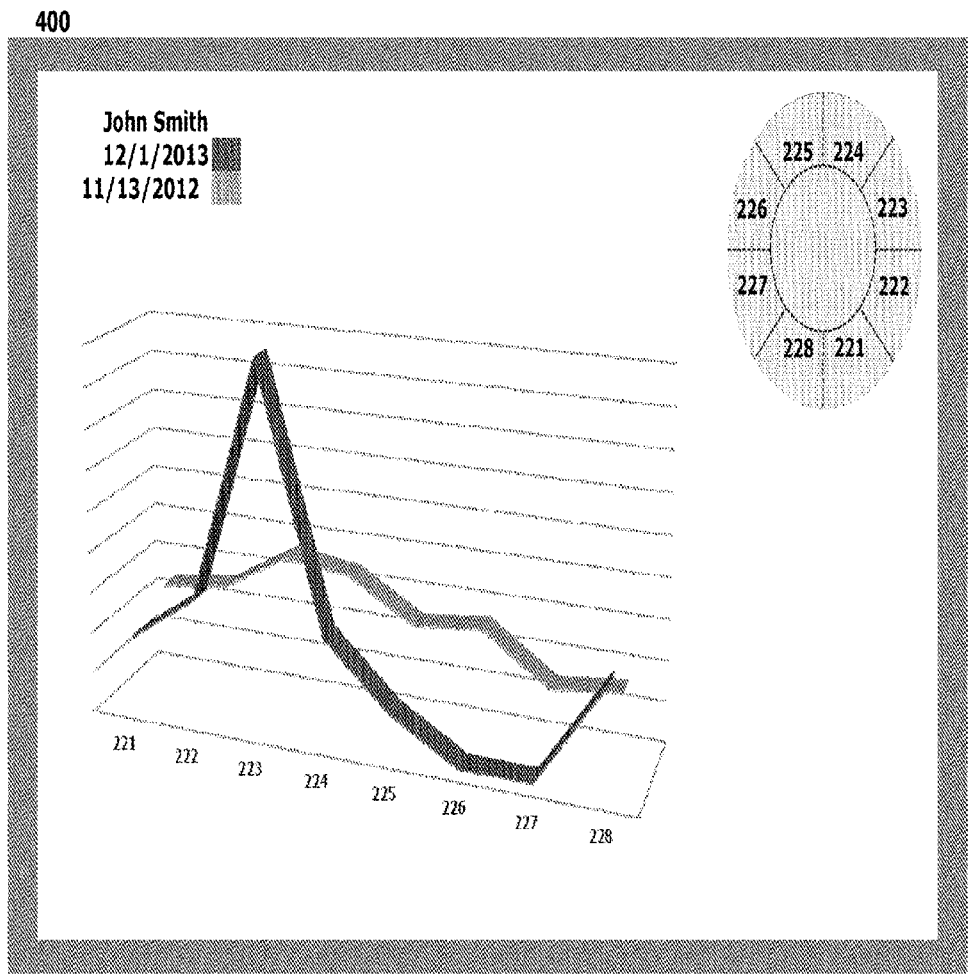
FIG. 4J is an exemplary visual representation of information collected using a stability-assessing system in accordance with one aspect of the disclosed technology.
Figure 4K:
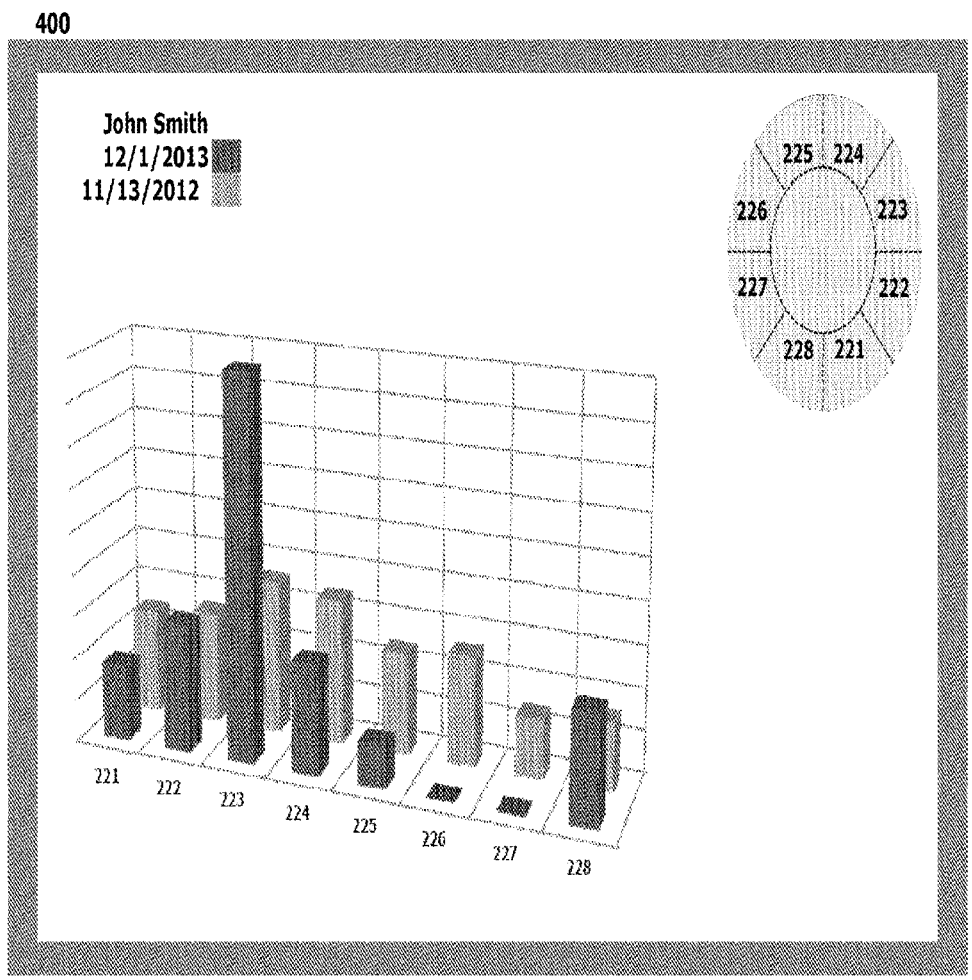
FIG. 4K is an exemplary visual representation of information collected using a stability-assessing system in accordance with one aspect of the disclosed technology.
Figure 4L:
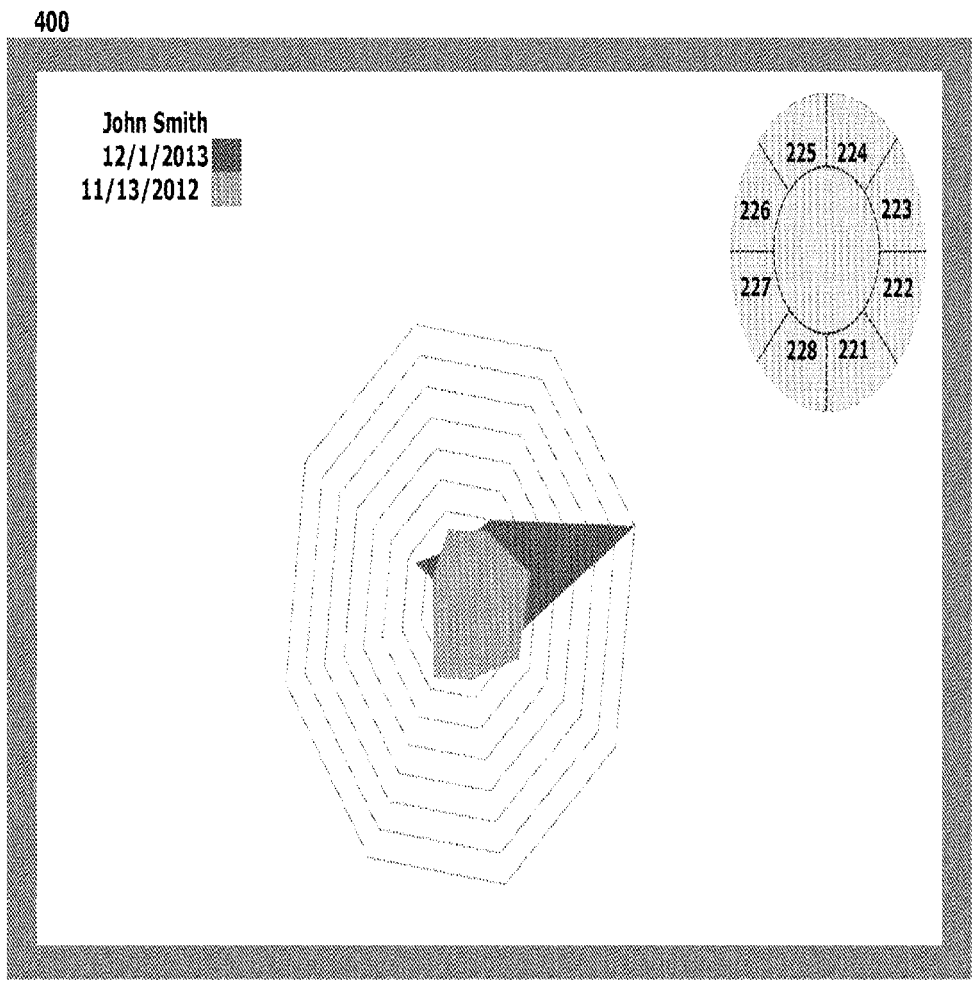
FIG. 4L is an exemplary visual representation of information collected using a stability-assessing system in accordance with one aspect of the disclosed technology.
Figure 4M:
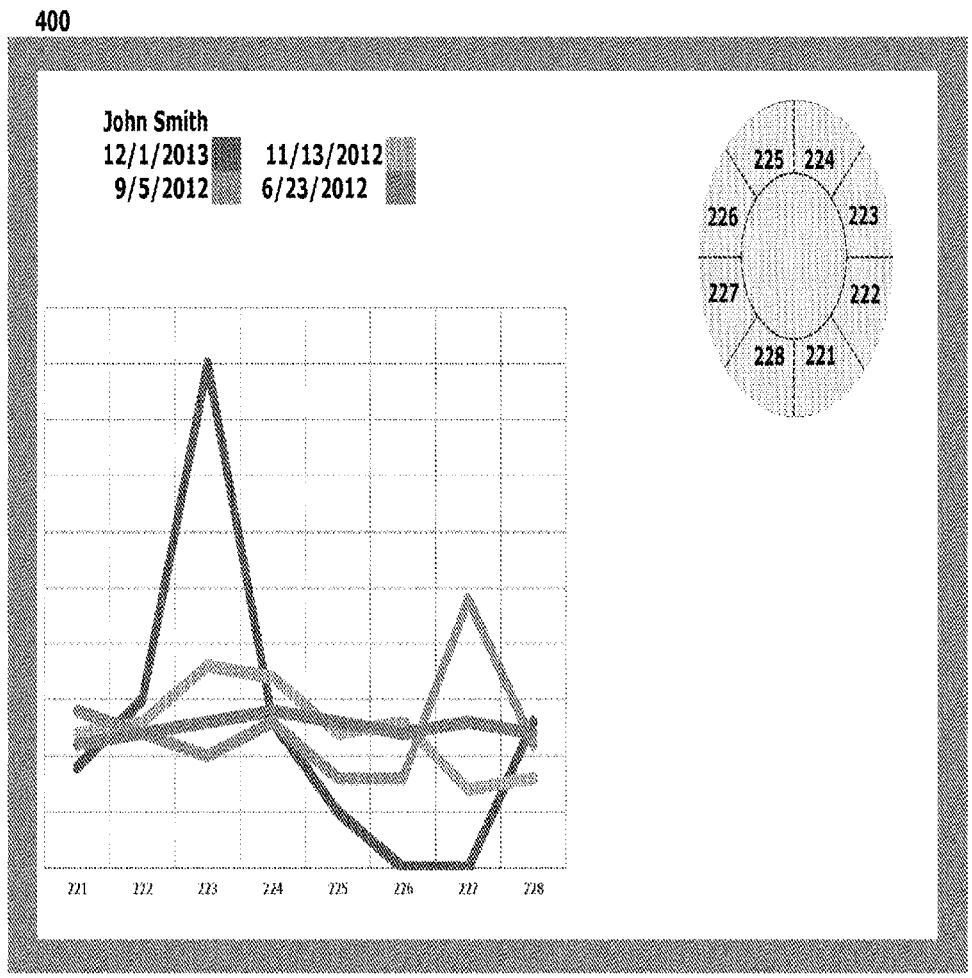
FIG. 4M is an exemplary visual representation of information collected using a stability-assessing system in accordance with one aspect of the disclosed technology.
Figure 4N:
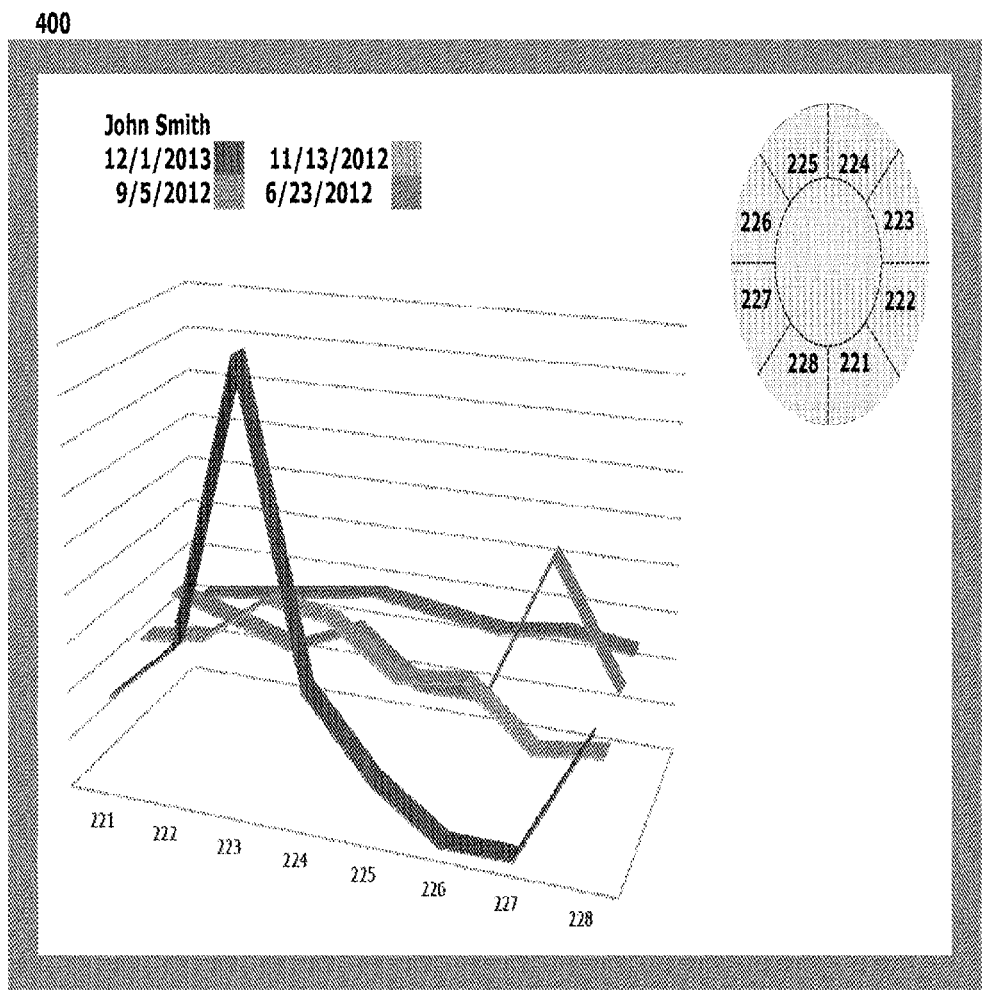
FIG. 4N is an exemplary visual representation of information collected using a stability-assessing system in accordance with one aspect of the disclosed technology.
Figure 40:
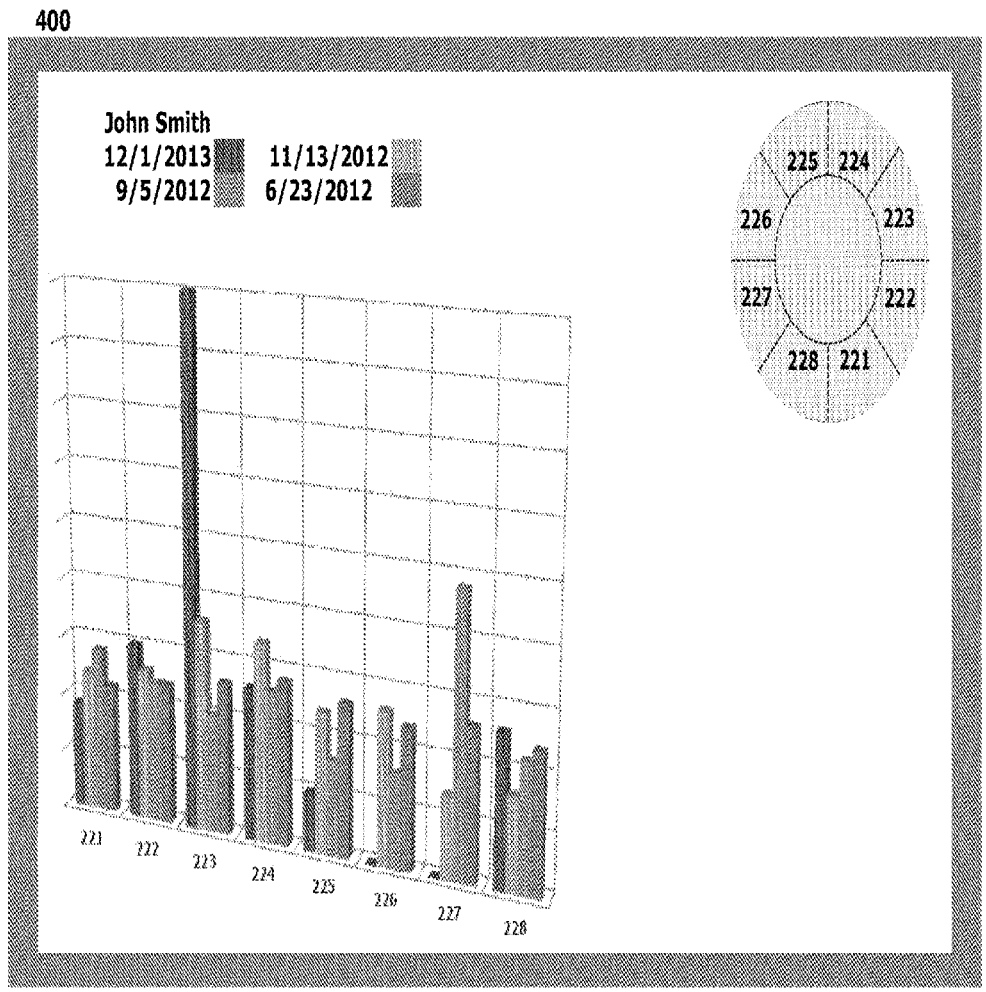
Figure 4P:
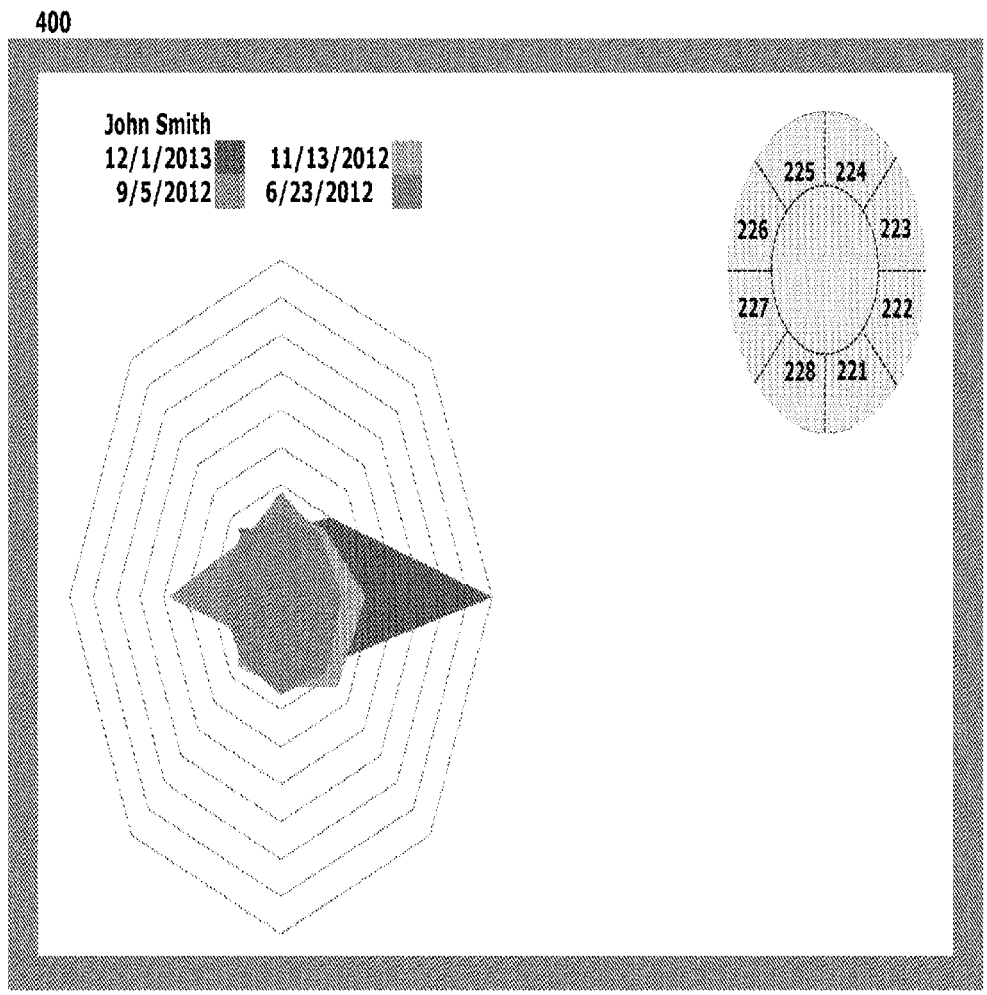
FIG. 4P is an exemplary visual representation of information collected using a stability-assessing system in accordance with one aspect of the disclosed technology.

It will be appreciated that the stability-assessing device and system described above can be used in a number of different applications without departing from the scope of the present invention. For example, FIG. 4E illustrates a visual representation of data collected for a hypothetical patient on two different dates. It will be appreciated that the comparisons of this data will provide users with valuable information regarding the current condition and/or progress of a patient with respect to a number of conditions. It will be appreciated that the exemplary visual representations shown in FIGS. 4E-4L show comparisons of data collected using the stability-assessing system for a hypothetical patient on two different dates.

FIG. 4M-FIG. 4P are exemplary visual representations of stability data collected for a hypothetical patient on four different dates using the stability-assessing system described above.

The system 100 can be used to in a method 500 to analyze, indicate, determine and/or otherwise evaluate an injury, a weakness, improvement, and/or deterioration of muscle and/or brain functions. In this method 500, the person 110 balances on the platform 200 with both feet, the right foot, and/or the left foot. Depending on the method 500, the person 110 balance with his or her eyes opened or closed.

During a method 500, the zone-by-zone parameters are gathered, via the sensors 231-238, and conveyed to the processor 300. The processor 300 interprets these parameters and sends an output to the display 400. The display 440 can then display graphics showing the zone-to-zone results in a meaningful manner.

The method 500 can be used to evaluate neuromuscular and/or proprioception weakness. Exercises and/or stretches can then be tailored to particularly work this muscle group. For example, if the graphics show a concentration in zone 224, this could indicate that the lateral malleolus muscle group needs to be strengthened. If the graphics instead show a concentration in zone 228, this could indicate that the peroneal muscle group should be the focus. If the graphics show a concentration in zone 221, this could indicate that the anterior and/or tibial posterior groups are relevant.

The person 110 could then plan an exercise program focused on the specified muscle group. Such a method 500 could be used to rehabilitate an injury. And/or a method 500 could be used to identify an injury-vulnerable area so that exercising can be done preventively.

The system 100 can also be used to test the integrity of muscles, ligaments, and joints.

The system 100 can additionally or alternatively be used to evaluate treatment modality. Much of the above discussion involves the avoidance of the zones 221-228 touching the ground. However, testing of the ability of the person 110 to deliberate touch the horizontal surface 120 with a particular zone can also provide useful information. In a treatment modality method 500, the person 110 can be verbally instructed as to the desired touch-to-ground zone. Another option would be to install LED lights or other indicators on the board 200 and use these to instruct the person 110.

A person/participant would be required through a strengthening program (either standing or sitting down) with one or two feet to use the board to touch the ground. This is different compared to the board's other function which is having the participant try and keep the board suspended in air/not touching for as long as possible. This application would have the participant touch the ground a certain of "X" amount of times. The board's 8 LED lights which are located (N,S,E,W,NE,NW,SE,SW) would light up and that would be an indication of where the participant could touch. This light-up sequence can be manually put in through an application or you can have a program that can program the amount of touches (or time duration you want the participant to use the board for) and the lights can go off one at a time in a random assortment.

Figure 5A:
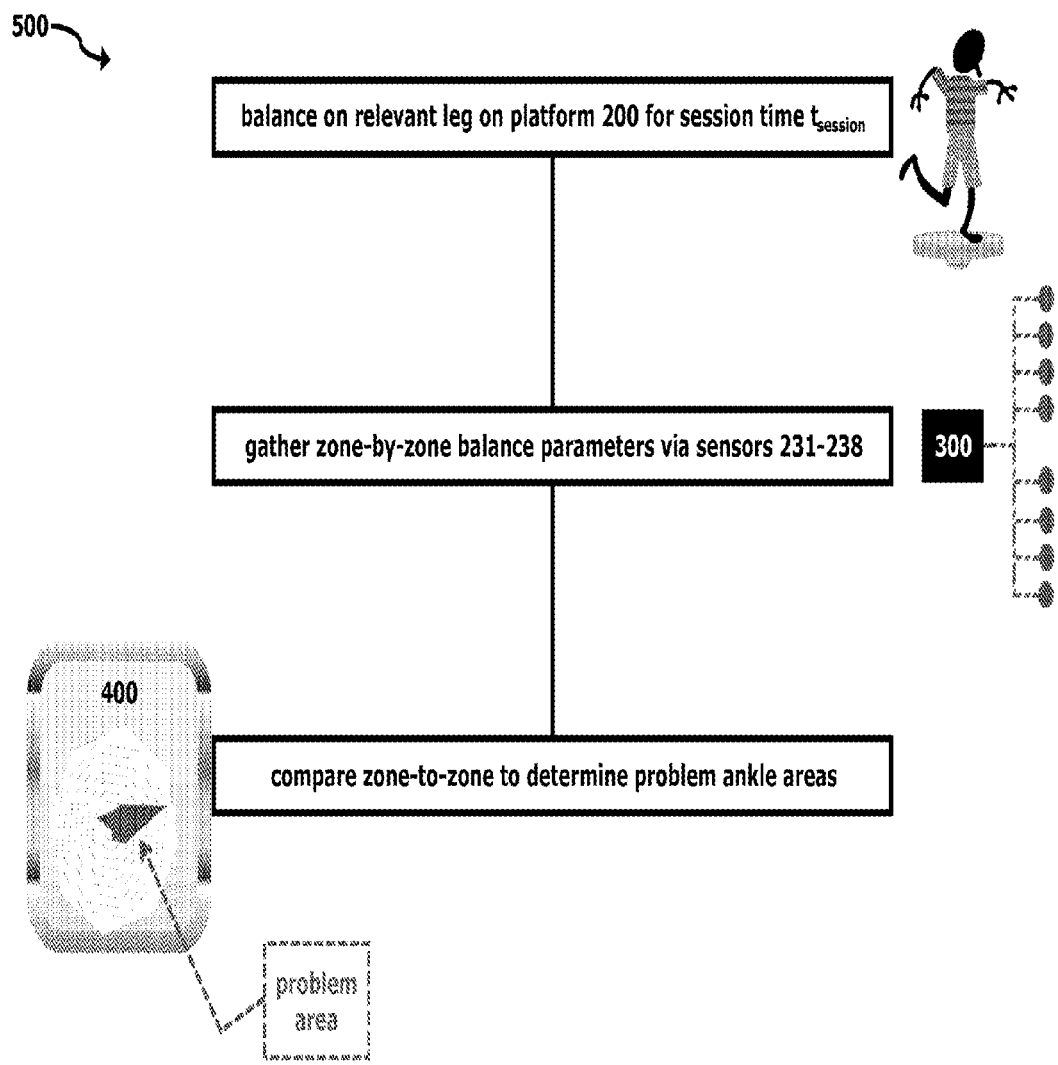
FIG. 5A is a flow diagram illustrating a method of assessing stability in accordance with one aspect of the disclosed technology.
Figure 5B:
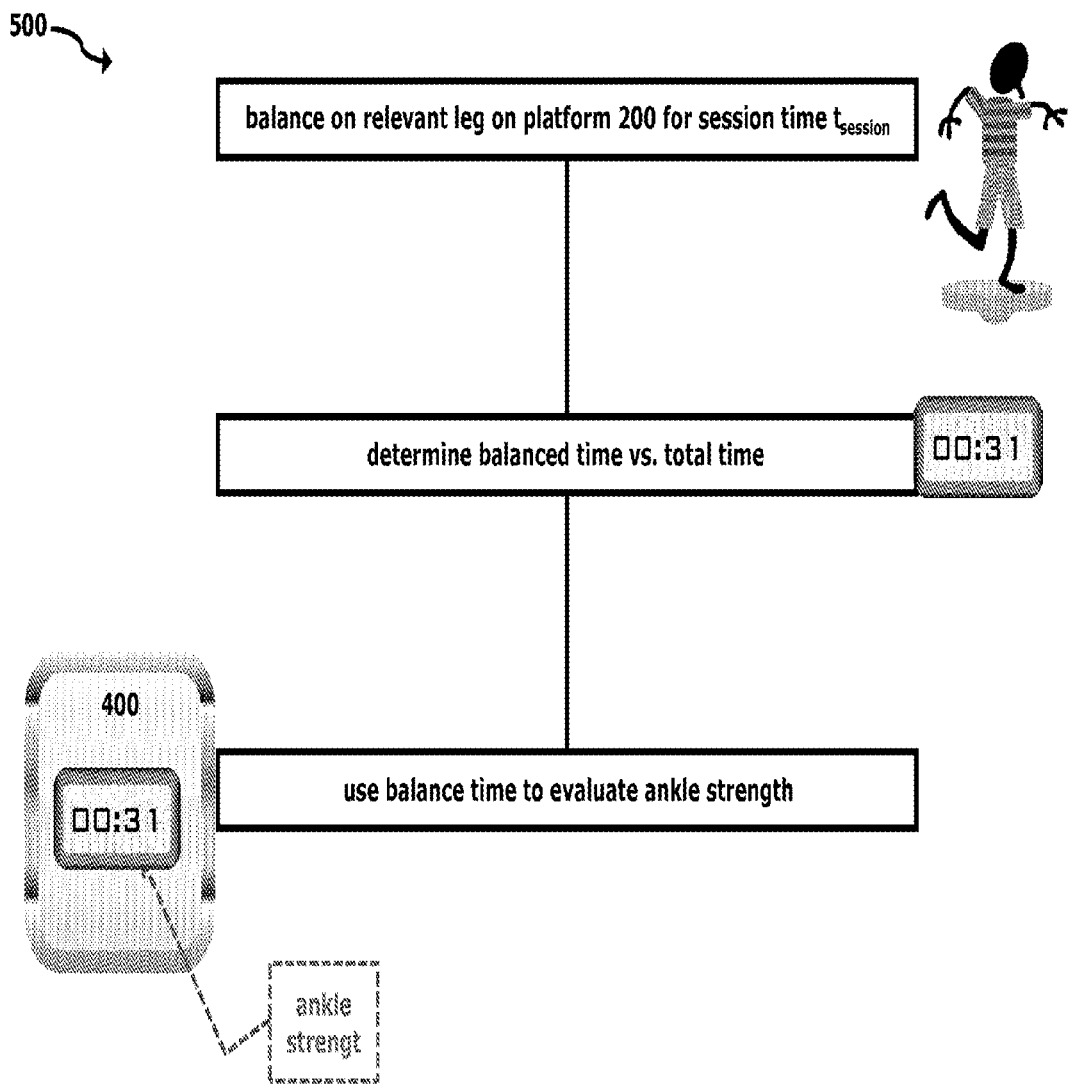
FIG. 5B is a flow diagram illustrating a method of assessing stability in accordance with one aspect of the disclosed technology.
Figure 5C:
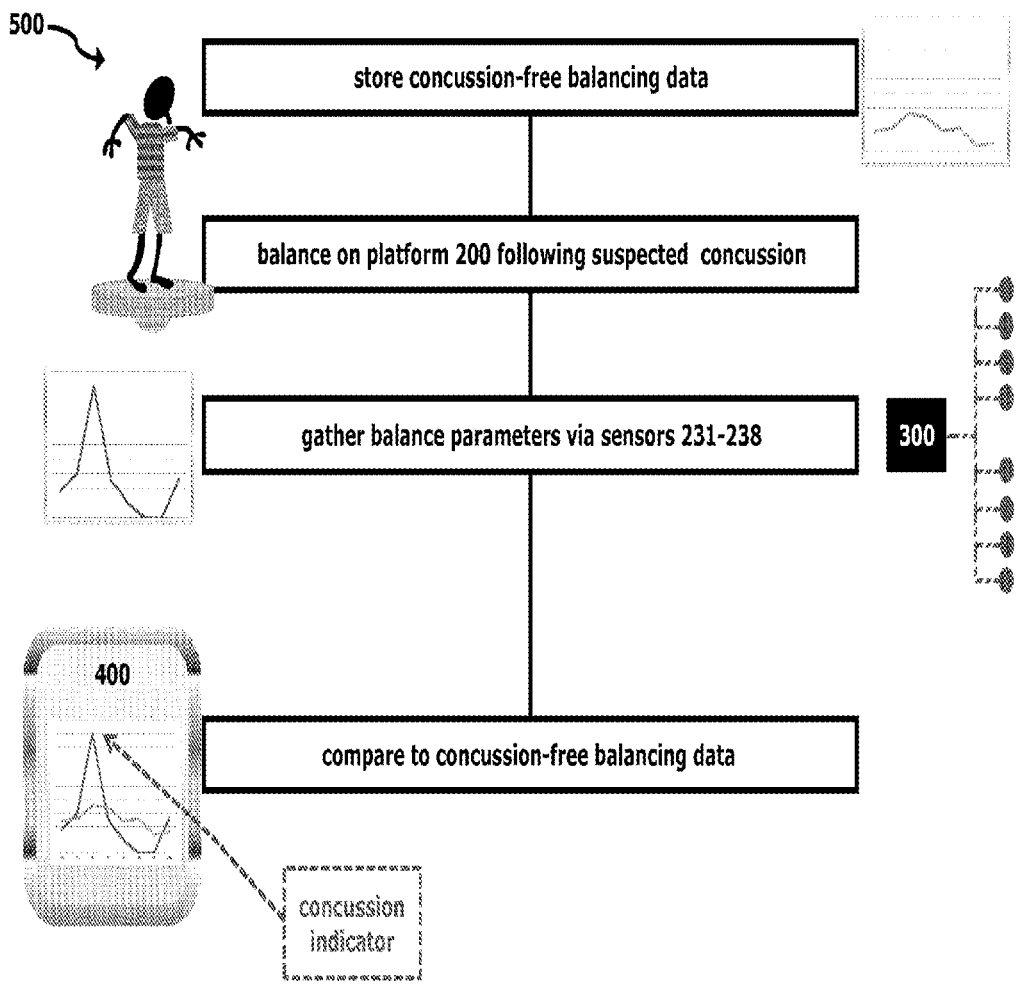
FIG. 5C is a flow diagram illustrating a method of assessing stability in accordance with one aspect of the disclosed technology.

The method 500 can also be used to quickly evaluate whether the person 110 has suffered a concussion. This concussion-evaluating method 500 can include the step of storing concession-free balancing data for the person 110. (FIG. 5C.) When a concussion is suspected, the person 110 balances on the platform 200 so that balance parameters can be gathered via sensors 231-238. This gathered data is then compared to the earlier concussion-free balancing data to indicate the likelihood of a concussion.

The method 500 allows a trainer, therapist, or other interested party to evaluate the person's proprioception and kinetic awareness (e.g., the awareness of time, grace, and body location either while standing or moving). In the past, this has been accomplished with a subject visual observation which is susceptible to human error.

Most injuries with ankles and lower body extremities are from non-impact mechanisms (concussion and head injuries are contact injuries, which obviously occur) so the system 100 looks to aid with inflexibility, loss of range of motion, strength imbalance, poor balance and/or poor technique.

Overcompensation is another factor causing injury; the system can give outputs on comparison on which muscles on each leg appropriate or misappropriate stability or functional effort. This is done by seeing in which quadrant, zone or segment of the board touches (i.e., Anterior, Anteromedial, Medial, Posteromedial, Posterior, Posterolateral, Lateral, Anterolateral).

It will be appreciated that trainers/doctors/therapists can use the counter of touches in a variety of ways, such as:

prescribing a set amount of time to use the board, regardless of touches; saying the participant has to use the board until they get "X" amount of touches or less in a prescribed time. Seeing how long a participant can use the board before they get "X" amount of touches Gathering data from the user's efforts on the board and seeing if there is an indication of ankle strength, proprioception, balance, mobility, etc. This could be done by using mathematical functions like mean, median, mode and range. This could track where the board is touching, the quantity of touching, give graphical or representative breakdown (or percentage breakdown) of which areas are being touched the most, how close the board is to the ground aka the tilt/tilt degree.

These numbers can be used to show with the tilt angles and degrees of the suspension in the air (or when the board isn't touching) which can be an indicator of ankle strength as it is not touching the ground as much OR the hopefully decreasing amount of touches with the idea that if the participant is touching the ground less frequently their ankle is getting stronger.

While aspects of the disclosed technology have been described with respect to stability assessment and collection of data associated with a participant's imbalance on the board, it will be appreciated that the device can also be configured and used in a performance or exercise-related mode of operation. For example, the processor or controller can communicate a predefined pattern to the visual indication configuration and the sensor configuration can then detect whether the user successfully completes the desired routine. In accordance with one embodiment, a program can be set or otherwise prescribed by a trainer, therapist, doctor or other clinician using the visual indicators. The controller or processor will communicate with the visual indicator such that the indicators associated with the various segments will activate or light up according to the predefined pattern. It will be appreciated that any number of patterns can be implemented without departing from the scope of the disclosed technology. Common touch patterns can include clockwise touching on a segment by segment basis, counterclockwise touching on a segment by segment basis, back and forth touching, side to side, or any other directional pattern.

In operation, when the user is balanced on the board, LEDs or other visual indicators associated with a given segment would light up or otherwise activate according to the predefined pattern. The user would then attempt to manipulate the board with his/her feet such that the perimeter portion associated with the desired segment would touch the ground or the platform would otherwise tilt to a predefined angle indicating that the user has successfully carried out movement according to the predefined plan. The sensor configuration would detect motion of the board as is discussed above with respect to stability-assessment and communicate this information to the processor or controller.

Figure 6A:
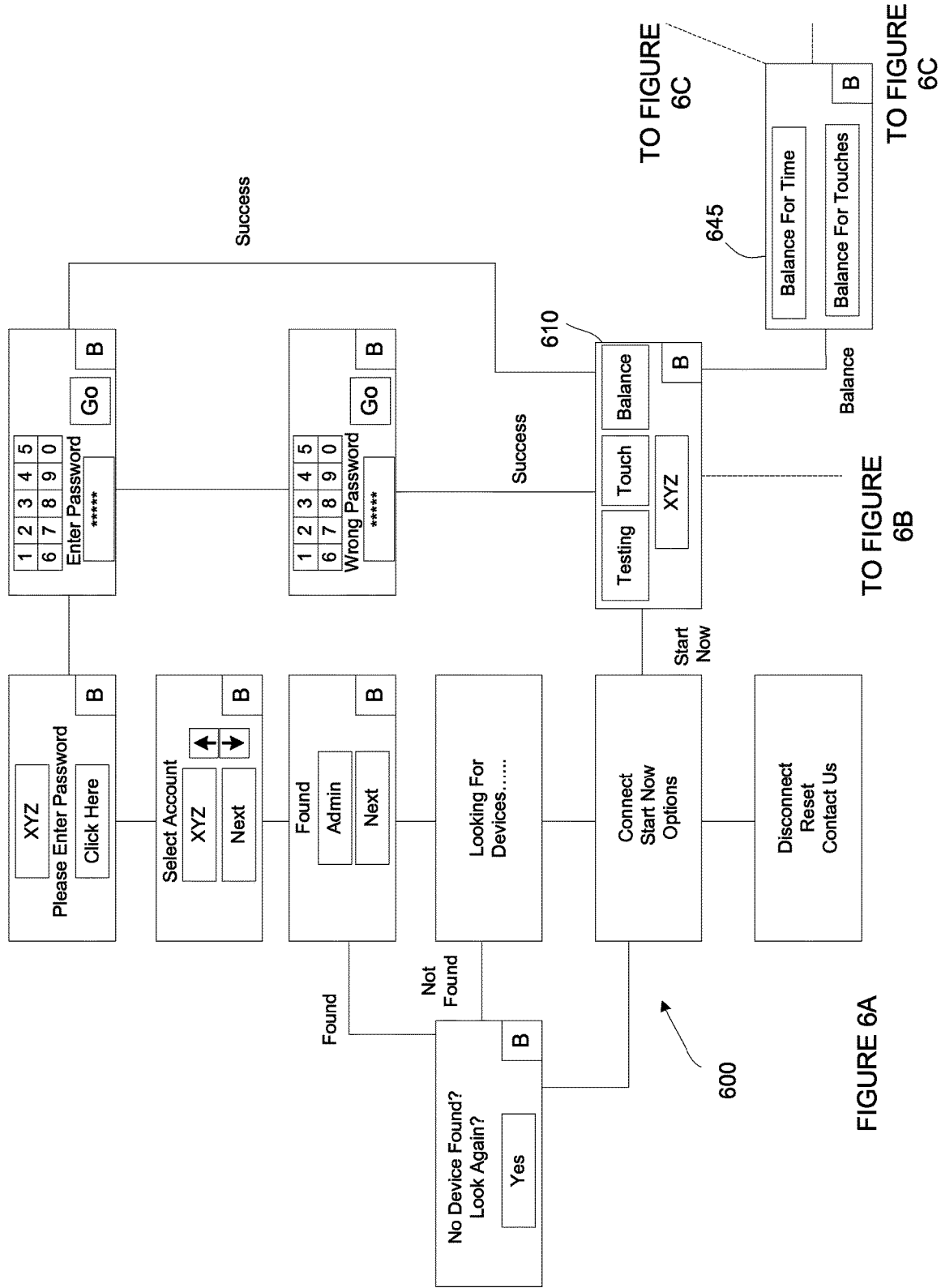
Figure 6B:
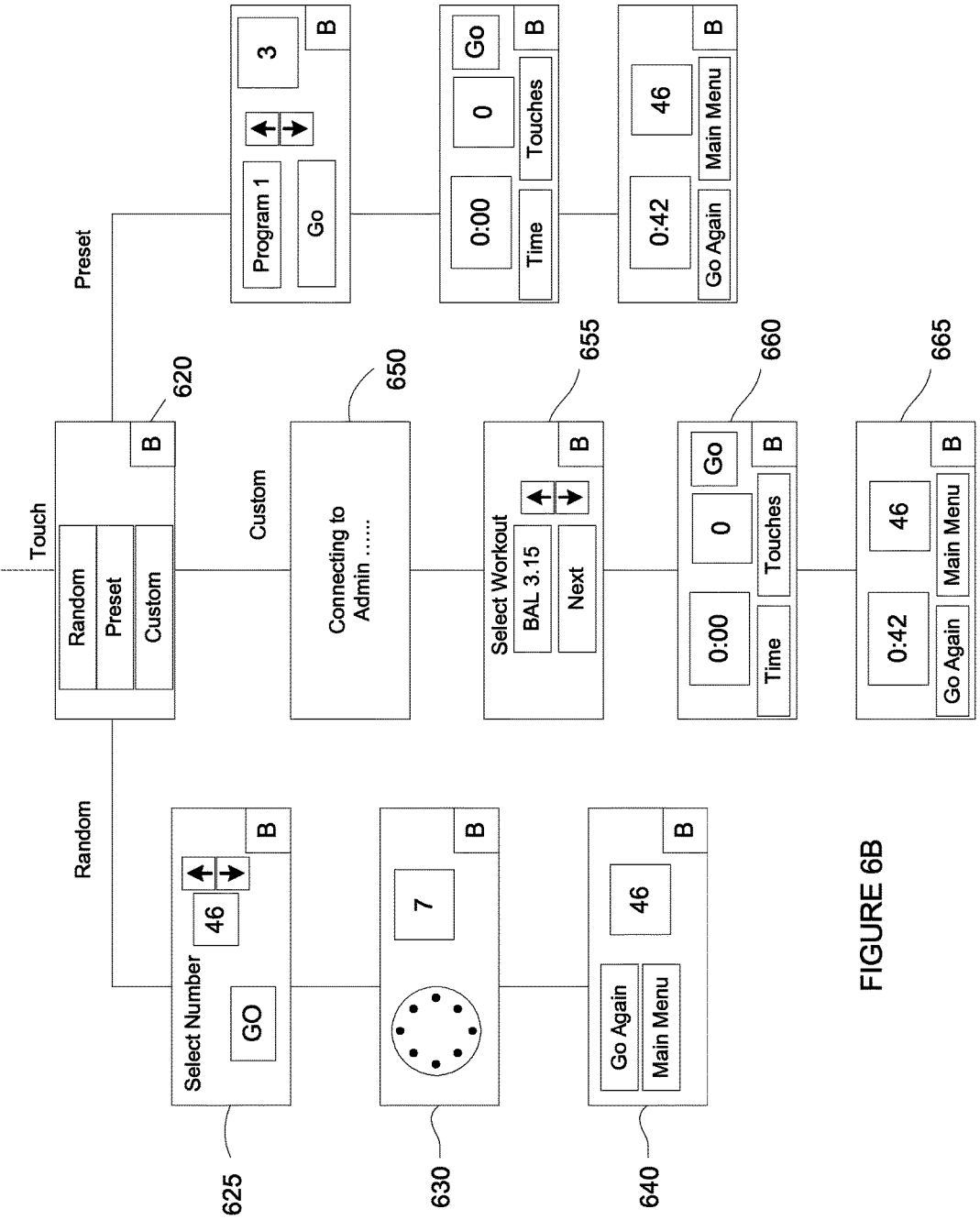

Referring now to FIGS. 6A-6C, a methodology for administering or otherwise operating the stability-assessing device is provided. At the outset, the stability-assessing device is powered up or otherwise activated 600. This can be accomplished in a number of ways within the scope of the disclosed technology. For example, the stability-assessing device can include a simple switch for activating power to the device. In addition, the device can be configured to include a push button start device for example. The device can be configured to include a separate push button located on the platform where the user can activate the push button using his/her feet. In this embodiment, the board can be configured to include audible indications such as a countdown that a sequence will be starting or that balance detection will be starting. Alternatively, the device can be configured to include a suitable touch display (e.g., an LCD touch display) such that the user can start or otherwise activate the device by interacting with the touch screen.

In accordance with one embodiment, the system can be configured with a "connect" feature that can be selected by the user such that the device will search via suitable wireless communication interface (e.g., blue tooth or Wi-Fi) for an administrator device with which to communicate. The administrative device can include a tablet, computer, laptop or smart phone. If an administrator account/device cannot be found, the user can prompt the device to search again if the device successfully locates and communicates with an administrator account and device, the name of the administrator account can show up on the display integrated within the device. The user can then navigate through input commands on the touch screen in the manner described more fully below. In the event that the device is in an area with multiple administrator accounts/devices, the user will have the option to choose which administrator account/device with which to communicate. The administrator's device can be configured to include a visual representation of the dashboard by way of software on their selected device to create an account that will be stored on software as a service or what is commonly known as cloud network or virtualization platform. The user can toggle through the accounts on the administrator's network to find the one he or she desires. With the selected account displayed, the user can interact to enter a password or other authentication credentials.

Block 610 shows a display representative of a successful password attempt. On the activity dashboard, the testing function can be used for baseline testing (for establishing a baseline), mid-season testing and post therapy/season testing. This sequence can be used when a therapist, trainer or other clinician recommends that a participant is ready to leave his or her training/therapy program. The touch program is indicative of a program where the participant and administrator will want the board to touch the ground (for example as part of rehab training) The "balance" program is the standard program for stability assessment. Block 620 indicates a random for a random spot generator. The user or administrator may choose how many touches they want and the platform can randomly choose one of the segments for the user to touch the ground. Block 625 is representative of a screen where the user can select the number. Block 630 is representative of a screen that can be shown during use of the device. Block 635 also shows a representative screen showing that a spot or segment is lit up. Block 640 is representative of an end screen after the random program is finished.

Block 645 is representative of a screen where the user can choose a time increment in the balance feature where the user attempts to balance and keep the perimeter of the board from touching the ground. Block 650 shows a representative custom screen where over the wireless connection the device connects or otherwise establishes a wireless communication link with an administrator account. Block 655 is representative of a screen where a workout can be selected. This can be done through the dashboard feature which can be hosted online. Block 660 shows a representative screen while the user is using the device. Block 665 shows a representative screen after the user has completed a custom program. The user will have a number of options including to repeat the program or to enter the main menu.

Although the system 100, the platform 200, the processor 300, the display 400, and/or the methods 500 have been shown and described as having certain forms and fabrications, such portrayals are not quintessential and represent only some of the possible adaptations of the claimed characteristics. Other obvious, equivalent, and/or otherwise akin embodiments could instead be created using the same or analogous attributes In addition to what has been described above, it will be appreciated that the device and system can be used in a number of different applications. For example, an exemplary application can include the balance time to get to one minute of having the board in a balanced condition. Stated differently, the system can track how long it takes a participant to keep the board from touching the ground, i.e. in a balanced condition for one minute or some other predefined time interval. In this exemplary embodiment, every time the board touches the ground or reaches a predefined tilt condition the clock or timer would stop. Then when the board is not touching the ground or is below the predefined tilt condition the board restarts the counter. This operation would ensure that the time touching the ground is not counted in the time it takes to get to one minute of balanced condition. It will be appreciated that this can be used for baseline data as well as analysis. In this embodiment there are two time intervals that are tracked. The first time interval is continuous and keeps running from the start of the program to the end of the program. The second time interval includes the time that is discussed above, that is the time when the board is in a balanced condition.

Another exemplary application can include a count of time in the air versus time on the ground. In any given usage scenario, the platform can keep track of time in the air and time on the ground as well as the total elapsed time. It will be appreciated that this can be used to complement other features and for tracking. In this exemplary embodiment three time periods would be tracked, where the first time period is a continuously running clock during the entirety of the application, the second time period is the amount of time that the board is "in the air" or in a balanced condition and the third amount of time is the time that the board is in contact with the ground or inclined such that it is in unbalanced condition.

Another exemplary implementation includes tracking the total number of touches in any given usage session and dividing the total touches among the electronically-defined segments around the board. It will be appreciated that this application can be used to determine predisposition for an injury or recovery effort.

While the device, system and exemplary methodologies of use have been discussed with respect to a user standing on the device it will be appreciated that the device can be configured or otherwise used in an implementation where the user places his/her hands on the board for tracking wrist, shoulder and arm dispositions. In this exemplary application, the platform could be configured to include a pair of handles which can be permanently or removably coupled to the board.

It will be appreciated that the system can allow for advanced tracking and analyzing of a user's use of the device and patterns established during use of the device. For example, the system can track the first and last touched segment during a usage session. As another example, the most common two and three touch sequence or succession of touches can be tracked and analyzed with a ranking of every multiple touch sequence. As another example, the system can track which spots a user is most likely to touch and for how long they will stay in contact with the ground. Another analytical example includes how quickly or slowly it takes a user to go from a balanced condition (for example where the board is approximately parallel to the ground) to a position where a segment of the board is touching the ground. Another exemplary tracking embodiment includes how quickly or slowly the participant switches between their first ten, twenty, thirty or forty spots and the first three and last three spots along the perimeter of the board. Another exemplary tracking embodiment includes tracking how quickly a user was able to accomplish a double count (e.g., repeated touching of a segment). Another exemplary tracking embodiment includes how much time or how many touches in between does it take on average to come back to a specific spot. In addition to the exemplary applications and embodiments described above, it will be appreciated that the device and system herein can be used to track a number of different user scenarios and user histories.

Although the disclosed technology has been shown and described with respect to a certain preferred aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

What is claimed is:

1. A stability-assessing device for assessing the stability of a person relative to a horizontal surface, the device comprising:
    a platform having a generally planar top surface, the platform having a perimeter;
    a base disposed below and supporting the platform, the base having a generally non-planar bottom surface such that the platform will rotate in response to a weight imbalance on the platform;
    a sensing configuration integrated into the device, wherein the sensing configuration is configured to sense orientation and/or motion of the platform relative to the horizontal surface and to generate signals representative of the sensed orientation and/or motion of the platform relative to the horizontal surface, wherein the platform is electronically divided into zones around the perimeter of the platform; and
    a visual indicator configuration integrated into the device, wherein the visual indicator configuration is configured to provide selective visual indications to one or more of the electronically defined zones.

2. The stability-assessing device of claim 1, wherein the sensing configuration is configured to sense orientation and/or motion of each zone of the platform.

3. The stability-assessing device of claim 1, wherein the sensing configuration includes one or more sensors associated with each zone and configured to sense orientation and/or motion of each zone of the platform relative to the horizontal surface.

4. The stability-assessing device of claim 3, wherein the sensors include pressure sensors, force sensors, acceleration sensors, tilt sensors and/or bump sensors.

5. The stability-assessing device of claim 1, wherein the platform is electronically divided into at least four zones.

6. The stability-assessing device of claim 1, wherein the platform is electronically divided into at least eight zones.

7. The stability-assessing device of claim 1, wherein the sensor configuration is configured to detect when a portion of the perimeter of the platform corresponding to one of the electrically defined zones contacts the horizontal surface.

8. The stability-assessing device of claim 7, wherein the sensor configuration is configured to detect the force with which a portion of the perimeter of the platform corresponding to one of the electrically defined zones contacts the horizontal surface.

9. The stability-assessing device of claim 1, wherein the sensor configuration includes a plurality of sensors within the platform configured to detect a person's weight distribution when the user is on the platform.

10. A stability-assessing device for assessing the stability of a person relative to a horizontal surface, the device comprising:
    a platform having a generally planar top surface, the platform having a perimeter;
    a base disposed below and supporting the platform, the base having a generally non-planar bottom surface such that the platform will rotate in response to a weight imbalance on the platform;
    a sensing configuration integrated into the device, wherein the sensing configuration is configured to sense orientation and/or motion of the platform relative to the horizontal surface and to generate signals representative of the sensed orientation and/or motion of the platform relative to the horizontal surface, wherein the platform is electronically divided into zones around the perimeter of the platform; and a visual indicator configuration integrated into the device, wherein the visual indicator configuration is configured to provide selective visual indications to one or more of the electronically defined zones, wherein the visual indication configuration includes a light-emitting diode (LED) assembly associated with each of the electronically defined zones.

11. The stability-assessing device of claim 1, further comprising: a controller operatively coupled to the sensing configuration and the visual indicator configuration, wherein the controller is configured to provide command signals to the visual indicator configuration, and to receive signals from the sensing configuration.

12. The stability-assessing device of claim 11, wherein the controller is configured to provide a command signal to the visual indicator configuration associated with a given zone upon receiving a signal from the sensing configuration indicative of a sensed orientation with respect to the given zone.

13. The stability-assessing device of claim 1, further comprising a display positioned in the platform.

14. The stability-assessing device of claim 13, wherein the display is a touch-sensitive display.

15. The stability-assessing device of claim 11, further comprising a wireless communication interface operatively coupled to the controller.

16. A stability-assessing system comprising the stability-assessing device of claim 15 and a remote display, wherein the stability assessing device is in wireless data communication with the remote display.

17. The stability-assessing system of claim 16, wherein the controller is programmed to convert input from the sensor configuration into balance characteristics particular to each zone.

18. A balance board for use by a person on a horizontal surface, the balance board comprising:
   a platform having a generally planar top surface, the platform having a perimeter;
   a base disposed below and supporting the platform, the base having a generally non-planar bottom surface such that the platform will rotate in response to a weight imbalance on the platform;
   a plurality of sensors integrated into the balance board, wherein the plurality of sensors are configured to sense orientation and/or motion of the platform relative to the horizontal surface and to generate signals representative of the sensed orientation and/or motion of the platform relative to the horizontal surface;
   wherein the platform is electronically divided into zones around the perimeter of the platform;
   and a visual indicator configuration integrated into the device, wherein the visual indicator configuration is configured to provide selective visual indications to one or more of the electronically defined zones.

19. The balance board of claim 18, wherein the visual indication configuration includes a light-emitting diode (LED) assembly associated with each of the electronically defined zones.

20. The balance board of claim 18, further comprising:
   a controller operatively coupled to the plurality of sensors and the visual indicator configuration, wherein the controller is configured to provide command signals to the visual indicator configuration, and to receive signals from the plurality of sensors, the command signals resulting in selective visual indications in one or more of the zones, and to receive signals from the plurality of sensors.

21. The balance board of claim 20, wherein the controller is configured to provide command signals to the visual indicator configuration in a predefined pattern.

22. The balance board of claim 18, further comprising a display positioned in the platform.

23. The balance board of claim 18, further comprising a wireless communication interface operatively coupled to the controller.

* * * * *